United States Patent
Kumar et al.

(10) Patent No.: US 10,889,548 B2
(45) Date of Patent: Jan. 12, 2021

(54) COMPOSITIONS AND METHODS FOR INHIBITING DIHYDROOROTATE DEHYDROGENASE

(71) Applicant: Clear Creek Bio, Inc., Cambridge, MA (US)

(72) Inventors: Vikram S. Kumar, Boston, MA (US); David P. Hesson, Malvern, PA (US); Ping Huang, Shanghai (CN); Mo Jia, Shanghai (CN); Xianjun You, Shanghai (CN)

(73) Assignee: Clear Creek Bio, Inc., Cambridge, MA (US)

( * ) Notice: Subject to any disclaimer, the term of this patent is extended or adjusted under 35 U.S.C. 154(b) by 0 days.

(21) Appl. No.: 16/364,446

(22) Filed: Mar. 26, 2019

(65) Prior Publication Data

US 2019/0292154 A1  Sep. 26, 2019

Related U.S. Application Data

(60) Provisional application No. 62/682,440, filed on Jun. 8, 2018, provisional application No. 62/655,407, filed on Apr. 10, 2018, provisional application No. 62/648,320, filed on Mar. 26, 2018.

(51) Int. Cl.
    *C07D 215/52*    (2006.01)
(52) U.S. Cl.
    CPC ................... *C07D 215/52* (2013.01)
(58) Field of Classification Search
    CPC .................................................. C07D 215/52
    See application file for complete search history.

(56) References Cited

U.S. PATENT DOCUMENTS

| | | | |
|---|---|---|---|
| 3,674,774 A | 7/1972 | Williams et al. | |
| 3,802,999 A | 4/1974 | Williams et al. | |
| 4,166,452 A | 9/1979 | Generales, Jr. | |
| 4,256,108 A | 3/1981 | Theeuwes | |
| 4,265,874 A | 5/1981 | Bonsen et al. | |
| 4,284,786 A | 8/1981 | Kammerer et al. | |
| 4,451,648 A | 5/1984 | Parsons et al. | |
| 4,680,299 A * | 7/1987 | Hesson ............... | C07D 215/52 514/311 |
| 5,032,597 A | 7/1991 | Hesson | |
| 5,523,408 A | 6/1996 | Batt et al. | |
| 5,679,709 A | 10/1997 | Bartlett et al. | |
| 5,807,876 A | 9/1998 | Armistead et al. | |
| 5,945,418 A | 8/1999 | Bemis et al. | |
| 6,093,742 A | 7/2000 | Salituro et al. | |
| 6,214,841 B1 | 4/2001 | Jackson et al. | |
| 6,344,465 B1 | 2/2002 | Armistead et al. | |
| 6,395,763 B1 | 5/2002 | Stamos et al. | |
| 6,399,773 B1 | 6/2002 | Liu et al. | |
| 6,410,540 B1 | 6/2002 | Goehring et al. | |
| 6,420,403 B1 | 7/2002 | Iwanowicz et al. | |
| 6,509,363 B2 | 1/2003 | Salituro et al. | |
| 6,518,291 B1 | 2/2003 | Saunders et al. | |
| 6,528,508 B2 | 3/2003 | Salituro et al. | |
| 6,541,496 B1 | 4/2003 | Armistead et al. | |
| 6,613,896 B1 | 9/2003 | Ramasamy et al. | |
| 6,617,323 B2 | 9/2003 | Iwanowicz et al. | |
| 6,617,324 B1 | 9/2003 | Naraian et al. | |
| 6,624,184 B1 | 9/2003 | Gu et al. | |
| 6,632,945 B2 | 10/2003 | Salituro et al. | |
| 6,635,644 B2 | 10/2003 | Salituro et al. | |
| 6,653,309 B1 | 11/2003 | Saunders et al. | |
| 6,825,224 B2 | 11/2004 | Stamos et al. | |
| 6,867,299 B2 | 3/2005 | Broadhurst et al. | |
| 6,919,335 B2 | 7/2005 | Iwanowicz et al. | |
| 6,967,214 B2 | 11/2005 | Armistead et al. | |
| 7,053,111 B2 | 5/2006 | Gu et al. | |
| 7,060,720 B2 | 6/2006 | Gu et al. | |
| 7,087,642 B2 | 8/2006 | Stamos et al. | |
| 7,125,898 B2 | 10/2006 | Aston et al. | |
| 7,135,575 B2 | 11/2006 | Munson et al. | |
| 7,169,779 B2 | 1/2007 | Salituro et al. | |
| 7,205,324 B2 | 4/2007 | Gu et al. | |
| 7,329,681 B2 | 2/2008 | Armistead et al. | |
| 7,423,047 B2 | 9/2008 | Brookings et al. | |

(Continued)

FOREIGN PATENT DOCUMENTS

| | | |
|---|---|---|
| WO | 99/32110 A1 | 7/1999 |
| WO | 2000050043 A1 | 8/2000 |

(Continued)

OTHER PUBLICATIONS

Amrutkar, 2017, Pancreatic Cancer Chemoresistance to Gemcitabine, Cancers 9(11):E157 (23 pages).
Angelov, 2009, Blood-Brain Barrier Disruption and Intra-Arterial Methotrexate-Based Therapy for Newly Diagnosed Primary CNS Lymphoma: A Multi-Institutional Experience, J Clin Oncol 27(21):3503-9 (8 pages).
Arteaga, 1989, Phase I Clinical and Pharmacokinetic Trial of Brequinar Sodium (DUP 785; NSC 368390), Cancer Research, 49:4648-53.
Ball, 2008, Acute GvHD: pathogenesis and classification, Bone Marrow Transplantation 41:S58-S64.
Batist, 1985, Phase I and pharmacokinetic study of tiazofurin (TCAR, NSC 286193) administered by continuous infusion. Invest New Drugs. 3(4):349-55.
Bennett, 1976, Proposals for the classification of the acute leukaemias. French-American-British (FAB) co-operative group Br. J. Haematol. 33 (4):451-8.

(Continued)

Primary Examiner — Timothy R Rozof
(74) Attorney, Agent, or Firm — Brown Rudnick LLP

(57) ABSTRACT

The invention provides therapeutic compositions that contain an inhibitor of dihydroorotate dehydrogenase (DHODH) and promote sustained elevation of dihydroorotate (DHO) levels in a patient. The compositions are useful for treating disorders associated with unregulated DHODH activity, such as acute myeloid leukemia. The invention also provides methods of determining therapeutically effective doses of compositions that contain a DHODH inhibitor. The invention further provides methods of synthesis of 2-(2'-halo-1-1'-biphenyl-4-yl)-quinoline carboxylic acids, which are useful as DHODH inhibitors.

6 Claims, 8 Drawing Sheets

(56) References Cited

U.S. PATENT DOCUMENTS

| | | |
|---|---|---|
| 7,425,555 B2 | 9/2008 | Angell et al. |
| 7,427,636 B2 | 9/2008 | Cannizzaro et al. |
| 7,432,290 B2 | 10/2008 | Stamos et al. |
| 7,521,447 B2 | 4/2009 | Munson et al. |
| 7,638,501 B1 | 12/2009 | Naviaux |
| 7,642,276 B2 | 1/2010 | Angell et al. |
| 7,777,069 B2 | 8/2010 | Stamos et al. |
| 7,989,498 B2 | 8/2011 | Saunders et al. |
| 8,410,160 B2 | 4/2013 | Fryszman et al. |
| 8,748,408 B2 | 6/2014 | Naviaux |
| 8,895,918 B2 | 11/2014 | Cooks et al. |
| 9,365,639 B2 | 6/2016 | Robinson et al. |
| 9,546,979 B2 | 1/2017 | Cooks et al. |
| 9,761,426 B2 | 9/2017 | Cooks et al. |
| 2002/0065296 A1 | 5/2002 | Dumas et al. |
| 2003/0232877 A1 | 12/2003 | Sikorski et al. |
| 2004/0224920 A1 | 11/2004 | Naviaux |
| 2010/0098678 A1 | 4/2010 | Naviaux |
| 2014/0031383 A1 | 1/2014 | Zon et al. |
| 2014/0235556 A1 | 8/2014 | Halse et al. |
| 2015/0328204 A1 | 11/2015 | Zon et al. |
| 2016/0046697 A1 | 2/2016 | Robinson et al. |
| 2017/0119880 A1 | 5/2017 | Clarke et al. |

FOREIGN PATENT DOCUMENTS

| | | |
|---|---|---|
| WO | 2004/096287 A2 | 11/2004 |
| WO | 2005117943 A2 | 12/2005 |
| WO | 2008030752 A2 | 3/2008 |
| WO | 2012052180 A1 | 4/2012 |
| WO | 2012109329 A2 | 8/2012 |
| WO | 2013049045 A1 | 4/2013 |
| WO | 2015122995 A1 | 8/2015 |
| WO | 2015169944 A1 | 11/2015 |
| WO | 2017/037022 A1 | 3/2017 |
| WO | 2017117372 A1 | 7/2017 |
| WO | 2018038886 A1 | 3/2018 |
| WO | 2018096538 A1 | 5/2018 |
| WO | 2019028171 A1 | 2/2019 |

OTHER PUBLICATIONS

Bennett, 1989, Proposals for the classification of chronic (mature) B and T lymphoid leukaemias. French-American-British (FAB) Cooperative Group J. Clin. Pathol. 42 (6):567-84.

Blackwell, 2017, The Role of Cancer-Derived Exosomes in Tumorigenicity & Epithelial-to-Mesenchymal Transition, Cancers, 9(8):105 (11 pages).

Bork, 1989, A Phase I Clinical and Pharmacokinetic Study of Brequinar Sodium, DUP 785 (NW 368390), Using a Weekly and a Biweekly Schedule, Eur J Cancer Clin Oncol, 25(10):1403-1411.

Bouchlaka, 2010, Immunotherapy following hematopoietic stem cell transplantation: potential for synergistic effects, Immunotherapy. 2(3):399-418.

Boven, 1992, The anti-tumour effects of the prodrugs N-I-leucyl-doxorubicin and vinblastine-isoleucinate in human ovarian cancer xenografts, Br J Cancer 66(6):1044-7.

Bruneau, 1998, Purification of human dihydro-orotate dehydrogenase and its inhibition by A77 1726, the active metabolite of leflunomide. Biochem J. 336(2):299-303.

Buj, 2018, Deoxyribonucleotide Triphosphate Metabolism in Cancer and Metabolic Disease, Front. Endocrinol. 9:177 (10 pages).

Burris, 1998, Pharmacokinetic and phase I studies of brequinar (DUP 785; NSC368390) in combination with cisplatin in patients with advanced malignancies, Invest. New Drugs, 16(1):19-27.

Chen, 1990, Structure-activity relationship of quinoline carboxylic acids. A new class of inhibitors of dihydroorotate dehydrogenase, Biochem. Pharmacol. 40:709-714.

Cho, 2017, Noninvasive Interrogation of Cancer Metabolism with Hyperpolarized 13C MRI, J Nucl Med 58:1201-1206.

Cuny, 2017, Inosine-5'-monophosphate dehydrogenase (IMPDH) inhibitors: a patent and scientific literature review (2002-2016), Expert Opin Ther Pat., 27(6):677-690.

Darvin, 2018, Immune checkpoint inhibitors: recent progress and potential biomarkers, Exp Mol Med. 50(12):165 (11 pages).

Di Gialleonardo, 2016, The Potential of Metabolic Imaging, Semin Nucl Med. 46(1):28-39.

Falini. 2010, New classification of acute myeloid leukemia and precursor-related neoplasms: changes and unsolved Issues Discov Med. 10(53):281-92.

Fedele, 2017, The Epithelial-to-Mesenchymal Transition in Breast Cancer: Focus on Basal-Like Carcinomas, Cancers, 9(10):E134 (19 pages).

Foo, 2014, Evolution of acquired resistance to anti-cancer therapy, J Theor Biol. 0:10-20 (24 pages).

Fu, 2017, The Emerging Role of Polo-Like Kinase 1 in Epithelial-Mesenchymal Transition and Tumor Metastasis, Cancers, 9(10):131 (15 pages).

Gaianigo, 2017, EMT and Treatment Resistance in Pancreatic Cancer, Cancers, 9(9):122 (17 pages).

Gebeyehu, 1985, Ribavirin, Tiazofurin, and Selenazofurin: Mononucleotides and Nicotinamide Adenine Dinucleotide Analogues. Synthesis, Structure, and Interactions with IMP Dehydrogenase, J. Med. Chem. 28:99-105.

Gnanamony 2017, Chemoresistance in pancreatic cancer: Emerging concepts, Oncology Letters 13:2507-2513.

Green, 1986, Clinical pharmacology of tiazofurin (2-β-D-ribofuranosylthiazole-4-carboxamide, NSC 286193), Invest New Drugs 4:387-394.

Grelet, 2017, Pleiotropic Roles of Non-Coding RNAs in TGF-β-Mediated Epithelial-Mesenchymal Transition and Their Functions in Tumor Progression, Cancers, 9(7):75 (15 pages).

Grem, 1990, Clinical toxicity associated with tiazofurin, Invest New Drugs. 8(2):227-38.

Groenendijk, 2014, Drug resistance to targeted therapies: Deja vu all over again, Mol. Oncol. 8:1067-1083 (17 pages).

Henriksen, 2015, The clearance concept with special reference to determination of glomerular filtration rate in patients with fluid retention, Clinical Physiology and Functional Imaging, 35(1):7-16.

Hsu, 2011, Measured GFR as Gold Standard—All that Glitters Is Not Gold?, Clinical Journal of the American Society of Nephrology, 6(8):1813-1814.

Jayaram, 1992, Int J Cancer, Clinical Pharmacokinetic Study of Tiazofurin Administered as a 1-hour infusion 51:182-188.

Kanu, 2008, Ion mobility-mass spectrometry, Journal of Mass Spectrometry, 43(1):1-22.

Kiewe, 2007 High-dose methotrexate is beneficial in parenchymal brain masses of uncertain originsuspicious for primary CNS lymphoma, Neuro Oncol. 9(2):96-102.

Kitchin, 1997, Rediscovering mycophenolic acid: A review of its mechanism, side effects, and potential uses Journal of the American Academy of Dermatology. 37(3):445-449.

Klymenko, 2017, Complex Determinants of Epithelial: Mesenchymal Phenotypic Plasticity in Ovarian Cancer, Cancers, 9(8):104 (32 pages).

Kolch 2005, Capillary electrophoresis-mass spectrometry as a powerful tool in clinical diagnosis and biomarker discovery, Mass Spectrom Rev. 24(6):959-77.

Koundinya, 2018, Dependence on the Pyrimidine Biosynthetic Enzyme DHODH Is a Synthetic Lethal Vulnerability in Mutant KRAS-Driven Cancers, Cell Chem Biol., 25(6):705-717.e11 (34 pages).

Lee, 2014, Current concepts in the diagnosis and management of cytokine release syndrome, (2014) Blood 124 (2):188-195.

Legras, 2017, Epithelial-to-Mesenchymal Transition and MicroRNAs in Lung Cancer, Cancers, 9(8):101 (29 pages).

Levey, 1999, A more accurate method to estimate glomerular filtration rate from serum creatinine: a new prediction equation. Modification of Diet in Renal Disease Study Group, Annals of Internal Medicine, 130(6):461-70.

Levey, 2009, A new equation to estimate glomerular filtration rate, Annals of Internal Medicine, 150(9):604-12.

(56) References Cited

OTHER PUBLICATIONS

Lu, 2017, Epithelial-to-Pericyte Transition in Cancer, Cancers, 9(7):77 (13 pages).
Malek, 2004, Effects of the IMPB-dehydrogenase inhibitor, Tiazofurin, in bcr-abl positive acute myelogenous leukemia, Leukemia Research, 28:1125-36.
Mani, 2007, Mesenchyme Forkhead 1 (FOXC2) plays a key role in metastasis and is associated with aggressive basal-like breast cancers, Proc Natl Acad Sci U S A. 104(24):10069-74.
Mansoori, 2017, The Different Mechanisms of Cancer Drug Resistance: A Brief Review, Adv Pharm Bull, 7(3):339-348.
Maroun, 1993, Multicenter phase II study of brequinar sodium in patients with advanced lung cancer. Cancer Chemother Pharmacol 32:64-66.
Marusyk, 2010, Tumor heterogeneity: causes and consequences, Biochim Biophys Acta. 1805(1):105-17.
Mathew, 2007, Chronic kidney disease and automatic reporting of estimated glomerular filtration rate: revised recommendations, The Medical Journal of Australia, 187(8):459-63.
Mathur, 2017, PTEN Regulates Glutamine Flux to Pyrimidine Synthesis and Sensitivity to Dihydroorotate Dehydrogenase Inhibition, Cancer Discov. 7(4):380-390 (p. 18).
Matsumoto, 2008, Low-field paramagnetic resonance imaging of tumor oxygenation and glycolytic activity in mice, J. Clin. Invest. 118(5):1965-1973 (10 pages).
Mele, 2000, The use of mycophenolate mofetil in transplant recipients, Immunopharmacology, 47:215-245.
Melink, 1985, Phase I Evaluation and Pharmacokinetics of Tiazofurin (2-beta-D-ribofuranosylthiazole-4-carboxamide, NSC 286193), Cancer Res. Jun. 1985;45(6):2859-65.
Miloushev, 2016, Hyperpolarization MRI: Preclinical Models and Potential Applications in Neuroradiology, Top Magn Reson Imaging 25(1):31-37.
Murray, 2013, Assessment of Glomerular Filtration Rate Measurement with Plasma Sampling: A Technical Review, J Nucl Med Technol. 41(2):67-75.
Natale, 1992, Multicenter phase II trial of brequinar sodium in patients with advanced melanoma, Ann Oncol. 3(8):659-60.
Nefedova, 2007, Mechanism of All-Trans Retinoic Acid Effect on Tumor-Associated Myeloid-Derived Suppressor Cells, Cancer Res. 67(22):11021-8.
Noe, 1990, Phase I and pharmacokinetic study of brequinar sodium (NSC368390), Cancer Res., 50(15):4595-99.
Obeng, 1997, Pharmacokinetics of tiazofurin in dogs, Biopharm Drug Dispos. 8(2):125-32.
Ohnesorge, 2005, Quantitation in capillary electrophoresis-mass spectrometry, Electrophoresis. 26(21):3973-87.
Paranjape, 2016, Inhibition of FOXC2 restores epithelial phenotype and drug sensitivity in prostate cancer cells with stem-cell properties, Oncogene. 35(46):5963-5976.
Peters, 1990, In vivo inhibition of the pyrimidine de novo enzyme dihydroorotic acid dehydrogenase by brequinar sodium (DUP-785; NSC 368390) in mice and patients, Cancer Res. 50(15):4644-9.
Pitt, 2009, Principles and Applications of Liquid Chromatography-Mass Spectrometry in Clinical Biochemistry, The Clinical Biochemist Reviews, 30(1):19-34.
Popsavin, 2011, Antitumour tiazofurin analogues embedded with an amide moiety at the C-2' position, Tetrahedron 67:6847-6858.
Popsavin, 2006, Synthesis and antiproliferative activity of two new tiazofurin analogues with 2'-amido functionalities, Bioorg. Med. Chem. Lett. 16(10):2773-2776.
Popsavin, 2016, Synthesis and in vitro antitumor activity of tiazofurin analogues with nitrogen functionalities at the C-2' position, European Journal of Medicinal Chemistry 111:114-125.
Preisler, 1987, Comparison of Three Remission Induction Regimens and Two Postinduction Strategies for the Treatment of Acute Nonlymphocytic Leukemia: A Cancer and Leukemia Group B Study, Blood, 69(5):1441-1449.
Rashidi, 2016, Maintenance therapy in acute myeloid leukemia: an evidence-based review of randomized trials, Blood 128(6):763-773.
Roche, 2017, Epigenetic Regulation of the Epithelial to Mesenchymal Transition in Lung Cancer, Cancers, 9(7):E72 (14 pages).
Roche, 2018, The Epithelial-to-Mesenchymal Transition in Cancer, Cancers (Basel). 10(2):E52 (4 pages).
Rose, 1969, Measurement of glomerular filtration rate by inulin clearance without urine collection, BMJ, 2:91-3 (3 pages).
Rule, 2004, Using serum creatinine to estimate glomerular filtration rate: accuracy in good health and in chronic kidney disease, Annals of Internal Medicine, 141(12):929-37.
Rundqvist, 2013, Tumour oxygenation: implications for breast cancer prognosis, Intern Med 274:105-112.
Saleh, 2015, Synthesis of Isatine Derivatives Considering Pfitzinger Reaction Part I, International Journal of Science and Research 4(8):2083-89.
Sangshetti, 2014, Pfitzinger Reaction in the Synthesis of Bioactive Compounds—A Review, Mini-Reviews in Organic Chemistry, 11:1-26.
Schlenk, 2014, Post-remission therapy for acute myeloid leukemia, Haematologica, 99(11):1663-70.
Schwartsmann, 1990, Phase I study of Brequinar sodium (NSC 368390) in patients with solid malignancies, Cancer Chemother. Pharmacol., 25(5):345-351.
Schwartz, 1984, A simple estimate of glomerular filtration rate in full-term infants during the first year of life, The Journal of Pediatrics, 104(6):849-54.
Schwartz, 1976, A simple estimate of glomerular filtration rate in children derived from body length and plasma creatinine, Pediatrics, 58(2):259-63.
Shvekhgeimer, 2004. The Pfitzinger Reaction (Review). Chemistry of Heterocylcic Compounds 40(3):257-294.
Soveri, 2014, Measuring GFR: A Systematic Review, American Journal of Kidney Diseases. 64(3):411-424.
Swyryd, 1974, N-(Phosphonacetyl)-L-Aspartate, a Potent Transition State Analog Inhibitor of Aspartate Transcarbamylase, Blocks Proliferation of Mammalian Cells in Culture, J. Biol. Chem. 249(21):6945-6950.
Sykes, 2016, Inhibition of Dihydroorotate Dehydrogenase Overcomes Differentiation Blockade in Acute Myeloid Leukemia, Cell, 167:171-186.
Thierauf, 2017, Epithelial-to-Mesenchymal Transition in the Pathogenesis and Therapy of Head and Neck Cancer, Cancers, 9(7):e376 (13 pages).
Tobin, 2018, Targeting myeloid-derived suppressor cells using all-trans retinoic acid in melanoma patients treated with Ipilimumab, Int Immunopharmacol., 63:282-291.
Tricot, 1987, Hematological and biochemical action of tiazofurin (NSC 286193) in a case of refractory acute myeloid leukemia, Cancer Res. 47(18):4988-91.
Tricot, 1989, Biochemically directed therapy of leukemia with tiazofurin, a selective blocker of inosine 5'-phosphate dehydrogenase activity, Cancer Res. 49(13):3696-701.
Trump, 1985, Phase I clinical study with pharmacokinetic analysis of 2-beta-D-ribofuranosylthiazole-4-carboxamide (NSC 286193) administered as a five-day infusion, Cancer Res. 45(6):2853-58.
Veglia, 2018, Myeloid-derived suppressor cells coming of age, Nat Immunol. 19(2):108-119.
Vu. 2017 Regulation of EMT in Colorectal Cancer: A Culprit in Metastasis, Cancers, 9(12):171 (22 pages).
Weber, 2018, Myeloid-Derived Suppressor Cells Hinder the Anti-Cancer Activity of Immune Checkpoint inhibitors, Front in Immunol. 9:1310 (9 pages).
Weber, 2015, Toxicities of Immunotherapy for the Practitioner, Journal of Clinical Oncology, 33(18):2092-2099.
Werden, 2016, Phosphorylation of serine 367 of FOXC2 by p38 regulates ZEB1 and breast cancer metastasis, without impacting primary tumor growth, Oncogene, 35(46):5977-5988.
Yang, 2016, Downregulation of Foxc2 enhances apoptosis induced by 5-fluorouracil through activation of MAPK and AKT pathways in colorectal cancer, Onc. Letters 11(2):1549-1554.
Yin, 2018. Potential Mechanisms Connecting Purine Metabolism and Cancer Therapy, Front. Immunol., 9:1697 (8 pages).
Zhao, 2004, Measuring changes in tumor oxygenation, Methods Enzymol., 386:378-418.

(56) References Cited

OTHER PUBLICATIONS

International Search Report and Written Opinion dated Jul. 17, 2019, for International Patent Application PCT/US2019/023983 with International filing date Mar. 26, 2019. (12 pages).

* cited by examiner

COMPOSITIONS AND METHODS FOR INHIBITING DIHYDROOROTATE DEHYDROGENASE

CROSS-REFERENCE TO RELATED APPLICATIONS

This application claims the benefit of, and priority to, U.S. Provisional Application No. 62/648,320, filed Mar. 26, 2018; U.S. Provisional Application No. 62/655,407, filed Apr. 10, 2018; and U.S. Provisional Application No. 62/682,440, filed Jun. 8, 2018, the contents of each of which are incorporated herein by reference.

FIELD OF THE INVENTION

The invention relates generally to therapeutic compositions and methods.

BACKGROUND

Proliferating cancer cells show substantially different metabolic needs compared to normal differentiated cells as they require additional nutrients to support their high rates of proliferation. Success in targeting cancer cell metabolism will materialize from an improved understanding of exactly how cells control and consume nutrients into pathways that are essential for biosynthesis. As all cancer cells rely on this alteration in metabolism, these altered pathways represent strong therapeutic targets. However, discovering a therapeutic window between normal proliferating and cancer cells remains a major challenge as the metabolic requirements of these cells are similar. Thus, only a few molecules which target metabolic pathways have been established as a form of cancer treatment.

Brequinar is an example of a drug that can target metabolic pathways, particularly de novo biosynthesis of pyrimidine. However, this drug has failed in the past because it could not be delivered within an appropriate therapeutic window.

SUMMARY

The invention recognizes that brequinar has failed in the past because it has not been dosed to achieve optimal enzyme inhibition. The invention solves that problem by using a highly sensitive marker of target engagement, a metabolite, to tailor a patient's dose to get an optimal Time Above Threshold (therapeutic window). Unlike prior approaches, the claimed invention is based on measuring target engagement instead of drug metabolism. In that manner, proper dosing of brequinar is achieved to kill cancer cells without causing harmful and toxic side effects to patients.

The de novo biosynthesis of pyrimidine is an essential metabolic pathway for nucleic acid synthesis. Although most cells meet their needs for nucleotides by reutilizing current ones through the salvage pathway, activated T cells and other rapidly proliferating cells, namely cancer cells are highly dependent on de novo nucleotide synthesis. Dihydroorotate dehydrogenase (DHODH) is the fourth sequential and rate-limiting enzyme in the de novo biosynthesis pathway of pyrimidines and it is the only enzyme found within the mitochondrial inner membrane of eukaryotes. Inhibition of this enzyme leads to intense reductions in cellular pyrimidine pools and eventually results in the failure of cells to proliferate.

Aspects of the invention are accomplished by measuring a trough dihydroorotate (DHO) level before a dose and using that level to dose adjust. In the historic studies with brequinar, there was high variability in the pharmacokinetic parameters. To overcome this, previous drug developers used plasma brequinar levels as a way to dose adjust but were not able to find an optimal dose and schedule for the drug. In some patients, brequinar is metabolized quickly, and there is not enough time above threshold of enzyme inhibition (and DHO), and hence too low a dose that is safe but will not produce any therapeutic effect. If brequinar is dosed at higher doses to achieve a therapeutic effect, the concentration of the drug results in too much time above threshold, causing toxic effects to be observed in healthy cells.

The invention recognizes that measuring the DHO level provides an accurate indication of target engagement of brequinar. Accurately knowing target engagement allows for appropriate doses of brequinar to be achieved that maintains the dosing within the therapeutic window.

With this understanding, the invention further recognizes that brequinar, and more generally, inhibitors of dihydroorotate dehydrogenase, can be used to treat certain cancers, such as acute myeloid leukemia (AML). AML afflicts over a million people worldwide. AML is incurable in the majority of cases and accounts for 1.8% of cancer deaths in the United States. Although recent decades have seen advances in our ability to diagnose and classify cases of AML, progress in treatment of AML has been less forthcoming: 90% of AML cases are treated with a therapeutic strategy that has remain unchanged for over 40 years.

The insights of the invention provide new compositions and methods for treating such cancers. Mainly, DHODH is present in all leukemic cells (essential enzyme). Differential metabolic sensitivity between leukemic cells and normal cells (i.e., "Metabolic Therapeutic Window") presents a treatment opportunity. The compositions of the invention use inhibitors of dihydroorotate dehydrogenase (e.g., brequinar) on a novel dosing schedule to exploit the pro-differentiation effects and tolerability (lower dose with long exposure) between leukemic cells and normal cells. By linking the amount of DHODH inhibitor to the level of DHO, the compositions allow physicians to determine dosage of a drug based on engagement of the active pharmaceutical ingredient (API) with its target. Consequently, the compositions are optimized to achieve prolonged exposure to the API at a level sufficient to starve leukemic cells and to avoid the need for higher dosing that can harm other cells. The invention also provides methods of determining therapeutically effective doses of compositions that contain a DHODH inhibitor.

In addition to AML, the compositions and methods of the invention are more broadly useful for treating any diseases associated with unregulated or excessive DHODH activity, such as AML, arthritis, and multiple sclerosis. In particular, the compositions are useful for treating diseases that require sustained inhibition of DHODH. For example, recent studies have shown that the DHODH inhibitor brequinar decreases leukemia-initiating cell activity in mouse models of AML only when elevated levels of the compound are maintained in the plasma for extended periods.

The compositions and methods of the invention also enable physicians to tailor dosing regimens to individual patients. Because the rate of metabolism and elimination of a given drug varies among patients, the degree of target engagement by the API will differ among patients who have received the same drug and dosage. The level of DHO, however, is a universal indicator of DHODH inhibition across all patients. Thus, by monitoring levels of DHO in individual patients, the dose of a drug can be adjusted to achieve a desired level of DHODH inhibition on a case-by-case basis.

In an aspect, the invention provides compositions containing an inhibitor of DHODH in a therapeutically effective amount that raises or maintains a level of DHO above a threshold level in a subject for a period of more than 72 hours.

In an aspect, the invention provides compositions containing an inhibitor of DHODH in a therapeutically effective amount that results in a level of DHO being at least about 25 ng/mL in a subject.

In an aspect, the invention provides an oral formulation containing an inhibitor of DHODH in a therapeutically effective amount that raises or maintains a level of DHO above a threshold level in a subject for a period of more than 72 hours.

The threshold level of DHO may be measured in a sample obtained from a subject. The sample may be body fluid sample. For example, the body fluid may be plasma, blood, serum, urine, sweat, saliva, interstitial fluid, feces, or phlegm.

The threshold level of DHO may be a minimum level necessary for the DHODH inhibitor to provide a therapeutic benefit to a subject having a disorder. For example, the threshold level may be about 10 ng/mL, about 20 ng/mL, about 50 ng/mL, about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about 850 ng/mL, about 900 ng/mL, about 950 ng/mL, about 1000 ng/mL, about 1250 ng/ml, about 1500 ng/ml, about 1750 ng/ml, about 2000 ng/ml, about 2500 ng/ml, about 3000 ng/ml, about 3500 ng/ml, about 4000 ng/ml, about 4500 ng/ml, about 5000 ng/ml, about 6000 ng/ml, about 8000 ng/ml, about 10,000 ng/ml, about 12,000 ng/ml, about 15,000 ng/ml, about 20,000 ng/ml, about 25,000 ng/ml, about 30,000 ng/ml, about 40,000 ng/ml, about 50,000 ng/ml, about 75,000 ng/ml, about 100,000 ng/ml, about 150,000 ng/ml, about 200,000 ng/ml, about 300,000 ng/ml, or about 400,000 ng/ml.

The threshold level of DHO may be a maximum level above which a subject experiences one or more side effects of the DHODH inhibitor. For example, the threshold level may be about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about 850 ng/mL, about 900 ng/mL, about 950 ng/mL, about 1000 ng/mL, about 1250 ng/ml, about 1500 ng/ml, about 1750 ng/ml, about 2000 ng/ml, about 2500 ng/ml, about 3000 ng/ml, about 3500 ng/ml, about 4000 ng/ml, about 4500 ng/ml, about 5000 ng/ml, about 6000 ng/ml, about 8000 ng/ml, about 10,000 ng/ml, about 12,000 ng/ml, about 15,000 ng/ml, about 20,000 ng/ml, about 25,000 ng/ml, about 30,000 ng/ml, about 40,000 ng/ml, about 50,000 ng/ml, about 75,000 ng/ml, about 100,000 ng/ml, about 150,000 ng/ml, about 200,000 ng/ml, about 300,000 ng/ml, about 400,000 ng/ml, or about 500,000 ng/ml.

The threshold level of DHO may be a range of values. For example, the threshold level may from about 100 ng/mL to about 200 ng/mL, from about 150 ng/mL to about 200 ng/mL, from about 150 ng/mL to about 250 ng/mL, from about 200 ng/mL to about 250 ng/mL, or from about 200 ng/mL to about 300 ng/mL.

The DHODH inhibitor may be any agent that inhibits the activity of DHODH. The DHODH inhibitor may be a small molecule, protein, peptide, antibody, or polypeptide. The DHODH inhibitor may be brequinar, leflunomide, or teriflunomide. Brequinar may be in a modified form suitable for a therapeutic composition. For example, the DHODH inhibitor may be a brequinar analog, a brequinar derivative, a brequinar prodrug, a micellar formulation of brequinar, or a brequinar salt, such as a sodium salt.

The composition may contain the DHODH inhibitor at a defined amount. For example, the composition may contain brequinar sodium at about 400 mg/m$^2$, about 450 mg/m$^2$, about 500 mg/m$^2$, about 550 mg/m$^2$, about 600 mg/m$^2$, about 650 mg/m$^2$, about 700 mg/m$^2$, about 750 mg/m$^2$, or about 800 mg/m$^2$. The composition may contain another form of brequinar in amount equivalent to brequinar sodium at about 400 mg/m$^2$, about 450 mg/m$^2$, about 500 mg/m$^2$, about 550 mg/m$^2$, about 600 mg/m$^2$, about 650 mg/m$^2$, about 700 mg/m$^2$, about 750 mg/m$^2$, or about 800 mg/m$^2$.

The composition may be formulated for administration via a particular route. For example, the composition may be formulated for administration orally, intravenously, enterally, parenterally, dermally, buccally, topically, transdermally, by injection, subcutaneously, nasally, pulmonarily, or with or on an implantable medical device The composition may contain a second therapeutic agent. The second therapeutic agent may inhibit a target other than DHODH. For example, the second agent may inhibit a glutaminase, the PI3K pathway, or orotidine 5'-monophosphate (OMP) decarboxylase.

The therapeutically effective amount of the DHODH inhibitor may be an amount sufficient to raise or maintain a level of DHO in a subject to ameliorate, reduce, or eliminate one or more signs or symptoms of a disorder in the subject. The therapeutically effective amount of the DHODH inhibitor may be an amount sufficient to raise or maintain a level of DHO in a subject above a threshold level, such as a threshold level described above. The therapeutically effective amount of the DHODH inhibitor may be an amount sufficient to raise or maintain a level of DHO in a subject for a period of time, such as 72 hours, 84 hours, 96 hours, 5 days, 6 days, 7 days, 10 days, 2 weeks, or more.

The therapeutically effective amount of the DHODH inhibitor may be an amount that does not result in the subject developing a side effect. For example, the therapeutically effective amount of the DHODH inhibitor may be an amount that does not result in the subject developing one or more of a blood disorder, nausea, vomiting, stomatitis, mucositis, skin rash, phlebitis, photosensitivity reactions, angioneurotic edema, and localized secondary hyperpigmentation of inflamed skin.

The composition may be provided as a single unit dosage. The composition may be provided as divided dosages.

In an aspect, the invention provides methods of determining a therapeutically effective dose of a DHODH inhibitor to be provided to a subject to treat a disorder. The therapeutically effective dose inhibits DHODH to an extent that at least one sign or symptom of the disorder is reduced or eliminated. The methods include determining a therapeutically effective dose of a DHODH inhibitor based on a measured level of DHO in a sample from a subject.

The therapeutically effective dose of the DHODH inhibitor may be a dose that raises or maintains a level of DHO above a threshold level in a sample obtained from the subject for a period of more than 72 hours. The threshold level may be any threshold level, such as those described above. The sample may be any sample, such as those described above.

In an aspect, the invention provides methods of adjusting a dosing regimen of a DHODH inhibitor to treat a disorder in a subject that is currently on the dosing regimen. The methods include receiving information regarding a measured level of dihydroorotate (DHO) in a sample from a subject, comparing the received information to a reference that provides an association of a measured level of DHO with a recommended dosage adjustment of a DHODH inhibitor, and adjusting the dosing regimen of the DHODH inhibitor so that a next dose of the DHODH inhibitor in the dosing regimen results in a level of DHO being raised or maintained above a threshold level indicative that the amount of the DHODH inhibitor in the subject is sufficient to reduce or eliminate at least one sign or symptom of the disorder.

In the methods of determining a therapeutically effective dose of a DHODH inhibitor or adjusting a dosing regimen of a DHODH inhibitor, the DHODH inhibitor may be any DHODH inhibitor, such as those described above.

The disorder may be any disease, disorder, or condition for which a DHODH inhibitor would provide a therapeutic benefit. For example, the disorder may be cancer, such as leukemia (e.g., acute myeloid leukemia) or prostate cancer, or an autoimmune disease, such as multiple sclerosis or arthritis (e.g., rheumatoid arthritis or psoriatic arthritis).

The methods may include determining a time point when the therapeutically effective dose of the DHODH inhibitor should be provided to the subject. The methods may include providing the DHODH inhibitor to the subject at the therapeutically effective dose.

The recommended dosage adjustment may be an increase the dosage, decrease in the dosage, or no change in the dosage. The recommendation may include a value by which the dosage should be increased or decreased.

The information regarding a measured level of DHO in a sample from a subject may include a measured level from one sample obtained from the subject or measured levels from multiple samples obtained from the subject. The information may include a time point indicating when each sample was obtained from the subject.

The dosing regimen may be adjusted in any manner. For example, the dosing regimen may be adjusted by adjusting the dose, the time for delivering the dose, or both. The adjustment may include determining a time point for delivering the dose.

The methods may include providing the DHODH inhibitor to the subject at the determined dose. The DHODH inhibitor may be provided orally, intravenously, enterally, parenterally, dermally, buccally, topically, transdermally, by injection, subcutaneously, nasally, pulmonarily, or with or on an implantable medical device. The DHODH inhibitor may be provided as a single unit dosage, or it may be provided as divided dosages.

In an aspect, the invention provides methods of making a 2-(2'-halo-1-1'-biphenyl-4-yl)-quinoline carboxylic acid. The methods include incubating a compound of formula (I) with a compound of formula (II) in a mixture containing a base and adding an acid to the mixture, thereby creating a compound of formula (III) according to following reaction:

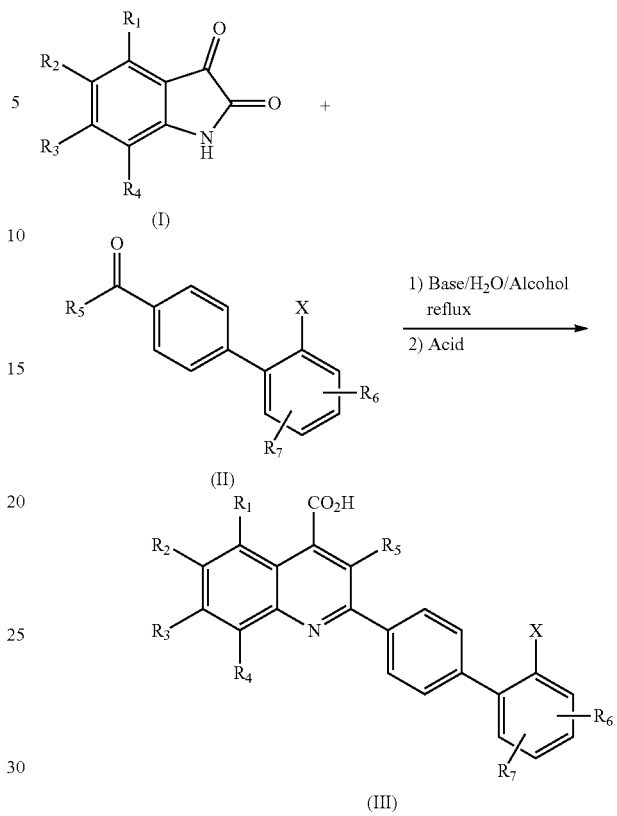

in which:
$R_1$, $R_2$, $R_3$, and $R_4$ are independently H, F, Cl, Br, I, $CH_3$, $CF_3$, $SCH_3$ or $CH_2CH_3$, at least two of $R_1$, $R^2$, $R_3$, and $R_4$ being H;
$R_5$ is H, alkoxy of 1-3 carbon atoms, or alkyl of 1-2 carbon atoms; $R_6$ and $R_7$ are independently H, F, Cl, Br, alkyl of 1-5 carbon atoms, $NO_2$, OH, $CF_3$ or $OCH_3$;
X is a halogen; and
the incubating step includes at least one of:
incubating the mixture at a temperature of from about 60° C. to about 70° C.,
the mixture containing a molar ratio of the base to the compound of formula (II) of from about 5:1 to about 8:1, and
incubating the mixture for from about 15 hours to about 30 hours.

The incubating step may include one or more of incubating the mixture at a temperature of from about 60° C. to about 70° C., using a mixture containing a molar ratio of the base to the compound of formula (II) of from about 5:1 to about 8:1, and incubating the mixture for from about 15 hours to about 30 hours.

The method may include a minimum yield of the compound of formula (III). For example, the yield of the compound of formula (III) may be at least 70%, at least 75%, at least 80%, at least 85%, at least 90%, or at least 95%.

The base may be any suitable base. For example, the base may be KOH, NaOH, or $NH_4OH$.

The alcohol may be any suitable alcohol. For example, the alcohol may be methanol, ethanol, 1-propanol, 2-propanol, butanol, 2-methyl-1-propanol, or pentanol.

The acid may be any suitable acid. For example, the acid may be HCl or acetic acid.

The compound of formula (III) may be brequinar. The compound of formula (III) may have the structure represented by formula (IV):

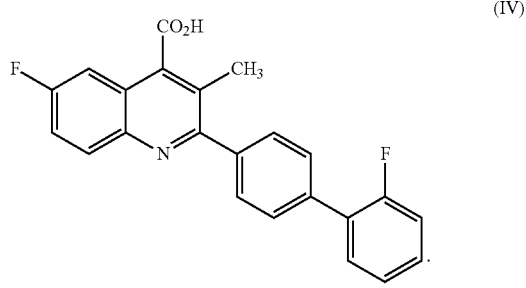 [SMILES: Cc1c(-c2ccc(-c3ccccc3F)cc2)nc2ccc(F)cc2c1C(=O)O ; "."]

(IV)

DETAILED DESCRIPTION

Figure 1:
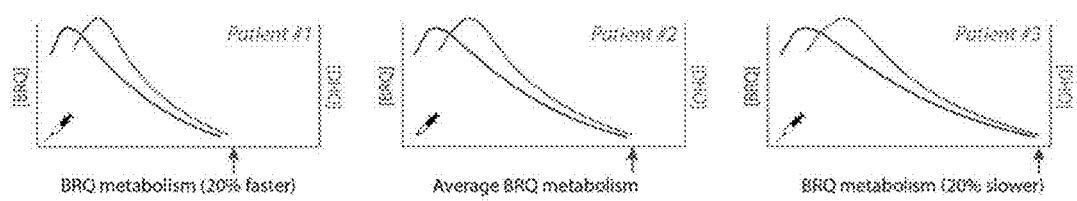
FIG. 1 is a series of graphs showing levels of brequinar and DHO in three patients that have received a single dose of brequinar according to the same dosing regimen.

The invention provides compositions and methods that promote sustained inhibition of dihydroorotate dehydrogenase (DHODH) in a patient. DHODH inhibitors are potentially useful drugs for treatment of cancer and autoimmune diseases. However, administration of some DHODH inhibitors to achieve therapeutic benefit is challenging due to the need to avoid doses that are toxic to healthy cells. Sustained inhibition of DHODH is required to provide a therapeutic benefit to the patient, but excessive inhibition is deleterious to normal tissues and leads to serious side effects. The invention overcomes this problem by providing compositions and methods in which the dosage of DHODH inhibitor in a given patient is determined based on the target engagement in the patient's body. Target engagement is assessed from measured levels of dihydroorotate (DHO), a substrate for DHODH, in samples obtained from the patient. By coupling dosing of the DHODH inhibitor to levels of DHO, the compositions and methods of the invention allow greater precision in dosing. Consequently, prolonged inhibition of DHODH can be attained without causing undue harm to healthy cells and tissue.

The compositions and methods of the invention are useful for treating diseases associated with unregulated or excessive DHODH activity, including cancer, such as acute myeloid leukemia (AML), and autoimmune diseases, such as arthritis, and multiple sclerosis. Although DHODH inhibitors have been previously been investigated for treatment of such diseases, the narrow therapeutic window of DHODH inhibitors has limited their utility as therapeutic agents to date. The compositions and methods of the invention unlock the therapeutic potential of potent DHODH inhibitors, such as brequinar.

The invention also provides methods for synthesis of brequinar and related compounds. By optimizing reaction conditions, such as stoichiometric ratios, temperature, and time, the methods of synthesis produce superior yields of desired products.

DHO as an Indicator of Target Engagement for DHODH Inhibitors

Methods of the invention include determining the dosage of a drug that contains a DHODH inhibitor based on a measured level of DHO in a sample obtained from a subject. DHO is an intermediate in the pyrimidine synthesis pathway. Pyrimidine biosynthesis involves a sequence of step enzymatic reactions that result in the conversion of glutamine to uridine monophosphate as shown below:

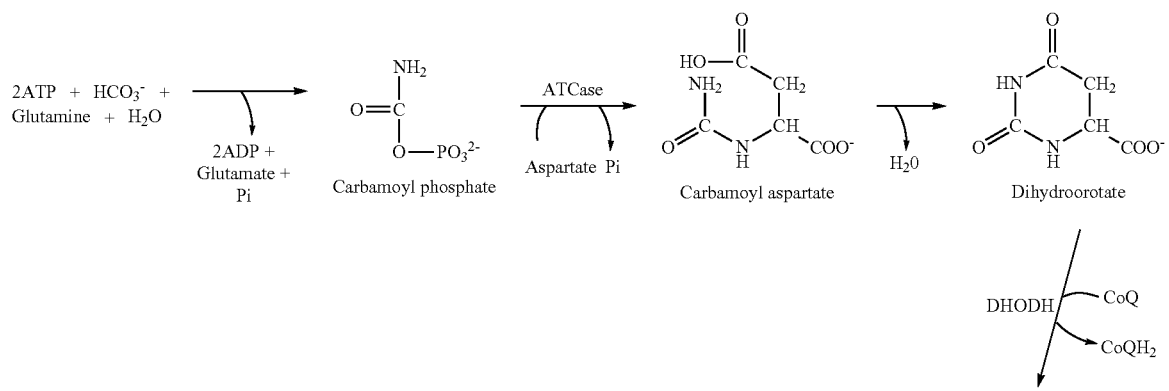

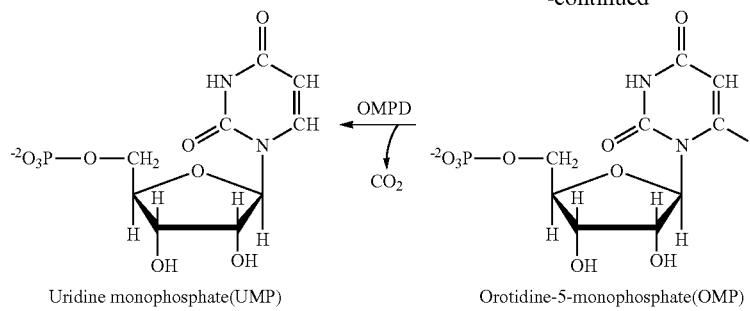
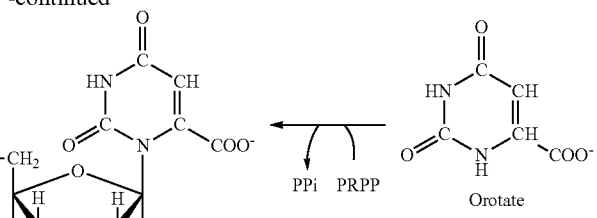

Uridine monophosphate(UMP)  Orotidine-5-monophosphate(OMP)  Orotate

Nucleotide synthesis pathways, such as the pyrimidine synthesis pathway, are of particular therapeutic interest. The high proliferation rate of cancer cells often places increased demand on nucleotide synthesis pathways. Consequently, enzymes that function in such pathways are useful targets for antineoplastic drugs. Specifically, drugs that inhibit enzymes require for nucleotide synthesis have been investigated for treating cancer. Therefore, levels of metabolites in nucleotide synthesis pathways are useful for evaluating the extent to which the APIs in such drugs are engaging their targets in vivo.

Several of the enzymes in the pyridine synthesis pathway are targets of drugs or drug candidates. For example, inhibitors of the following enzymes have been investigate as therapeutic agents: aspartate carbamoyltransferase (also known as aspartate transcarbamoylase or ATCase), which catalyzes the conversion of carbamoyl phosphate to carbamoyl aspartate; dihydroorotate dehydrogenase (DHODH), which catalyzes conversion of dihydroorotate (DHO) to orotate; and OMP decarboxylase (OMPD), which catalyzes conversion of orotidine monophosphate (OMP) to uridine monophosphate (UMP).

One element of the invention is recognition of the utility of DHO as an indicator of target engagement by DHODH inhibitors. One advantage of DHO is that cell membranes are permeable to the molecule. DHODH is localized to the mitochondrial inner membrane within cells, making direct measurement of enzyme activity difficult. However, DHO, which accumulates when DHODH is inhibited, diffuses out of cells and into the blood, which can be easily sampled. Another insight of the invention is that DHO is sufficiently stable that levels of the metabolite can be measured reliably. Previously, DHO was considered too unstable at ambient temperatures to be quantified accurately and was thus deemed unsuitable as an indicator of DHODH inhibition. However, the methods provided herein permit detection of DHO in plasma samples. Thus, by analyzing levels of DHO in blood or blood products, one can readily assess target engagement of a DHODH inhibitor.

Measuring the Level of DHO in a Sample

Methods of the invention include analysis of a measured level of DHO in a sample. The methods may include measurement of DHO.

In some embodiments, DHO is measured by mass spectrometry, optionally in combination with liquid chromatography. Molecules may be ionized for mass spectrometry by any method known in the art, such as ambient ionization, chemical ionization (CI), desorption electrospray ionization (DESI), electron impact (EI), electrospray ionization (ESI), fast-atom bombardment (FAB), field ionization, laser ionization (LIMS), matrix-assisted laser desorption ionization (MALDI), paper spray ionization, plasma and glow discharge, plasma-desorption ionization (PD), resonance ionization (RIMS), secondary ionization (SIMS), spark source, or thermal ionization (TIMS). Methods of mass spectrometry are known in the art and described in, for example, U.S. Pat. Nos. 8,895,918; 9,546,979; 9,761,426; Hoffman and Stroobant, Mass Spectrometry: Principles and Applications (2nd ed.). John Wiley and Sons (2001), ISBN 0-471-48566-7; Dass, Principles and practice of biological mass spectrometry, New York: John Wiley (2001) ISBN 0-471-33053-1; and Lee, ed., Mass Spectrometry Handbook, John Wiley and Sons, (2012) ISBN: 978-0-470-53673-5, the contents of each of which are incorporated herein by reference.

In certain embodiments, a sample can be directly ionized without the need for use of a separation system. In other embodiments, mass spectrometry is performed in conjunction with a method for resolving and identifying ionic species. Suitable methods include chromatography, capillary electrophoresis-mass spectrometry, and ion mobility. Chromatographic methods include gas chromatography, liquid chromatography (LC), high-pressure liquid chromatography (HPLC), and reversed-phase liquid chromatography (RPLC). In a preferred embodiment, liquid chromatography-mass spectrometry (LC-MS) is used. Methods of coupling chromatography and mass spectrometry are known in the art and described in, for example, Holcapek and Brydwell, eds. Handbook of Advanced Chromatography/Mass Spectrometry Techniques, Academic Press and AOCS Press (2017), ISBN 9780128117323; Pitt, Principles and Applications of Liquid Chromatography-Mass Spectrometry in Clinical Biochemistry, The Clinical Biochemist Reviews. 30(1): 19-34 (2017) ISSN 0159-8090; Niessen, Liquid Chromatography-Mass Spectrometry, Third Edition. Boca Raton: CRC Taylor & Francis. pp. 50-90. (2006) ISBN 9780824740825; Ohnesorge et al., Quantitation in capillary electrophoresis-mass spectrometry, Electrophoresis. 26 (21): 3973-87 (2005) doi:10.1002/elps.200500398; Kolch et al., Capillary electrophoresis-mass spectrometry as a powerful tool in clinical diagnosis and biomarker discovery, Mass Spectrom Rev. 24 (6): 959-77. (2005) doi:10.1002/mas.20051; Kanu et al., Ion mobility-mass spectrometry, Journal of Mass Spectrometry, 43 (1): 1-22 (2008) doi: 10.1002/jms.1383, the contents of which are incorporated herein by reference.

A sample may be obtained from any organ or tissue in the individual to be tested, provided that the sample is obtained in a liquid form or can be pre-treated to take a liquid form. For example and without limitation, the sample may be a blood sample, a urine sample, a serum sample, a semen sample, a sputum sample, a lymphatic fluid sample, a cerebrospinal fluid sample, a plasma sample, a pus sample, an amniotic fluid sample, a bodily fluid sample, a stool sample, a biopsy sample, a needle aspiration biopsy sample, a swab sample, a mouthwash sample, a cancer sample, a tumor sample, a tissue sample, a cell sample, a synovial fluid sample, a phlegm sample, a saliva sample, a sweat sample, or a combination of such samples. The sample may also be a solid or semi-solid sample, such as a tissue sample, feces sample, or stool sample, that has been treated to take a liquid form by, for example, homogenization, sonication, pipette trituration, cell lysis etc. For the methods described herein, it is preferred that a sample is from plasma, serum, whole blood, or sputum.

The sample may be kept in a temperature-controlled environment to preserve the stability of DHO. For example, DHO is more stable at lower temperatures, and the increased stability facilitates analysis of this metabolite from samples. Thus, samples may be stored at, or 4° C., −20° C., or −80° C.

In some embodiments, a sample is treated to remove cells or other biological particulates. Methods for removing cells from a blood or other sample are well known in the art and may include e.g., centrifugation, sedimentation, ultrafiltration, immune selection, etc.

The subject may be an animal (such as a mammal, such as a human). The subject may be a pediatric, a newborn, a neonate, an infant, a child, an adolescent, a pre-teen, a teenager, an adult, or an elderly patient. The subject may be in critical care, intensive care, neonatal intensive care, pediatric intensive care, coronary care, cardiothoracic care, surgical intensive care, medical intensive care, long-term intensive care, an operating room, an ambulance, a field hospital, or an out-of-hospital field setting.

The sample may be obtained from an individual before or after administration to the subject of a DHODH inhibitor. For example, the sample may be obtained 1 hour, 2 hours, 4 hours, 6 hours, 8 hours, 12 hours, 24 hours, 36 hours, 2 days, 3 days, 4 days, 5 days, 6 days, 7 days or more before administration of a DHODH inhibitor, or it may be obtained 1 hour, 2 hours, 4 hours, 6 hours, 8 hours, 12 hours, 24 hours, 36 hours, 2 days, 3 days, 4 days, 5 days, 6 days, 7 days or more after administration of a DHODH inhibitor.

Determining a Dosing Regimen

Methods of the invention include determining a dosing regimen of a DHODH inhibitor for a subject. The dosing regimen may include a dose, i.e., an amount, of the DHODH inhibitor that should be administered. The dosing regimen may include a time point for administration of a dose of the DHODH inhibitor to the subject. Because the dosing regimen is based on one or more measured levels of DHO in a sample obtained from the subject, the dosing regimen is tailored to an individual subject, e.g., a patient. Consequently, the methods of the invention provide customized dosing regimens that account for variability in pharmacokinetic properties, i.e., metabolism of the API by the subject, and pharmacodynamics properties, effect of the API on its target, among individuals.

The dosing regimen may be determined by comparing a measured level of DHO in a sample obtained from a subject to a reference that provides an association between the measured level and a recommended dosage adjustment of the DHODH inhibitor. For example, the reference may provide a relationship between administration of the DHODH inhibitor and levels of DHO in the subject. The relationship can be empirically determined from a known dose and time of administration of the DHODH inhibitor and measured levels of DHO at one or more subsequent time points. The reference may include a relationship between measured levels of the DHODH inhibitor or a metabolic product of the DHODH inhibitor and measured levels of DHO.

From the comparison between the measured level of DHO and the reference, a dosing regimen may then be determined. The dosing regimen may include a dosage of the DHODH inhibitor, a time for administration of the dosage, or both. The dosing regimen may be determined de novo, or it may comprise an adjustment to a previous dosing regimen, such as an adjustment in the dosage, the interval between administration of dosages, or both.

The dosing regimen is designed to deliver the DHODH inhibitor to the subject in an amount that achieves a therapeutic effect. The therapeutic effect may be a sign or symptom of a disease, disorder, or condition. The therapeutic effect may be inhibition of an enzyme in the metabolic pathway, or it may be a change in an indicator of inhibition of an enzyme in a metabolic pathway. The indicator may be DHO in the pathway, and the therapeutic effect may be an increase or decrease in levels of DHO. The therapeutic effect may be a decrease in number of cancer cells, a decrease in proliferation of cancer cells, an increase in differentiation of pre-cancerous cells, such as myeloblasts, complete remission of cancer, complete remission with incomplete hematologic recovery, morphologic leukemia-free stat, or partial remission. Increased differentiation of myeloblasts may be assessed by one or more of expression of CD14, expression of CD11b, nuclear morphology, and cytoplasmic granules.

The dosing regimen may ensure that levels of DHO are raised or maintained a minimum threshold required to achieve a certain effect. For example, the dosing regimen may raise or maintain levels of DHO above a threshold level in the subject for a certain time period. The time period may include a minimum, a maximum, or both. For example, the dosing regimen may raise or maintain levels of DHO above the threshold level for at least 6 hours, 12, hours, 24 hours, at least 48 hours, at least 72 hours, at least 84 hours, at least 96 hours, at least 5 days, at least 6 days, at least 7 days, at least 10 days, at least 2 weeks, or more. The dosing regimen may raise or maintain levels of DHO above the threshold level for not more than 24 hours, not more than 36 hours, not more than 48 hours, not more than 60 hours, not more than 72 hours, not more than 84 hours, not more than 96 hours, not more than 5 days, not more than 6 days, not more than 7 days, not more than 10 days, or not more than 2 weeks. The dosing regimen may raise or maintain levels of DHO above the threshold level for at least 72 hours but not more than 96 hours, for at least 72 hours but not more than 5 days, for at least 72 hours but not more than 6 days, for at least 72 hours but not more than 7 days, for at least 96 hours but not more than 7 days.

The dosing regimen may ensure that levels of DHO do not exceed or are maintained below a maximum threshold that is associated with toxicity. Levels of DHO above a maximum threshold may indicate that the DHODH inhibitor is causing or is likely to cause an adverse event in the subject. For example and without limitation, adverse events include abdominal pain, anemia, anorexia, blood disorder, constipation, diarrhea, dyspepsia, fatigue, fever, granulocytopenia, headache, infection, leukopenia, mucositis, nausea, pain at the injection site, phlebitis, photosensitivity, rash, somnolence, stomatitis, thrombocytopenia, and vomiting.

The dosing regimen may include a time point for administration of one or more subsequent doses to raise or maintain levels of DHO above a threshold level for a certain time period. The time point for administration of a subsequent dose may be relative to an earlier time point. For example, the time point for administration of a subsequent dose may be relative to a time point when a previous dose was administered or a time point when a sample was obtained from a subject.

The dosing regimen may include a schedule for administration of doses. For example, doses may be administered at regular intervals, such as every 24 hours, every 36 hours, every 48 hours, every 60 hours, every 72 hours, every 84 hours, every 96 hours, every 5 days, every 6 days, every week, every 2 weeks, every 3 weeks, or every 4 weeks. Alternatively, doses may be administered according to a schedule that does not require precisely regular intervals. For example, doses may be administered once per week, twice per week, three times per week, four times per week, once per month, twice per month, three times per month, four times per month, five times per month, or six times per month.

For example and without limitation, a dosing regimen for administration of a DHODH inhibitor, such brequinar, e.g., brequinar sodium, to a human subject may be as follows: 100 mg/m$^2$, administered intravenously twice weekly; 125 mg/m$^2$, administered intravenously twice weekly; 150 mg/m$^2$, administered intravenously twice weekly; 200 mg/m$^2$, administered intravenously twice weekly; 250 mg/m$^2$, administered intravenously twice weekly; 275 mg/m$^2$, administered intravenously twice weekly; 300 mg/m$^2$, administered intravenously twice weekly; 350 mg/m$^2$, administered intravenously twice weekly; 400 mg/m$^2$, administered intravenously twice weekly; 425 mg/m$^2$, administered intravenously twice weekly; 450 mg/m$^2$, administered intravenously twice weekly; 500 mg/m$^2$, administered intravenously twice weekly; 550 mg/m$^2$, administered intravenously twice weekly; 600 mg/m$^2$, administered intravenously twice weekly; 650 mg/m$^2$, administered intravenously twice weekly; 700 mg/m$^2$, administered intravenously twice weekly; 750 mg/m$^2$, administered intravenously twice weekly; 800 mg/m$^2$, administered intravenously twice weekly; 100 mg/m$^2$, administered intravenously every 72 hours; 125 mg/m$^2$, administered intravenously every 72 hours; 150 mg/m$^2$, administered intravenously every 72 hours; 200 mg/m$^2$, administered intravenously every 72 hours; 250 mg/m$^2$, administered intravenously every 72 hours; 275 mg/m$^2$, administered intravenously every 72 hours; 300 mg/m$^2$, administered intravenously every 72 hours; 350 mg/m$^2$, administered intravenously every 72 hours; 400 mg/m$^2$, administered intravenously every 72 hours; 425 mg/m$^2$, administered intravenously every 72 hours; 450 mg/m$^2$, administered intravenously every 72 hours; 500 mg/m$^2$, administered intravenously every 72 hours; 550 mg/m$^2$, administered intravenously every 72 hours; 600 mg/m$^2$, administered intravenously every 72 hours; 650 mg/m$^2$, administered intravenously every 72 hours; 700 mg/m$^2$, administered intravenously every 72 hours; 750 mg/m$^2$, administered intravenously every 72 hours; 800 mg/m$^2$, administered intravenously every 72 hours; 100 mg/m$^2$, administered intravenously every 84 hours; 125 mg/m$^2$, administered intravenously every 84 hours; 150 mg/m$^2$, administered intravenously every 84 hours; 200 mg/m$^2$, administered intravenously every 84 hours; 250 mg/m$^2$, administered intravenously every 84 hours; 275 mg/m$^2$, administered intravenously every 84 hours; 300 mg/m$^2$, administered intravenously every 84 hours; 350 mg/m$^2$, administered intravenously every 84 hours; 400 mg/m$^2$, administered intravenously every 84 hours; 425 mg/m$^2$, administered intravenously every 84 hours; 450 mg/m$^2$, administered intravenously every 84 hours; 500 mg/m$^2$, administered intravenously every 84 hours; 550 mg/m$^2$, administered intravenously every 84 hours; 600 mg/m$^2$, administered intravenously every 84 hours; 650 mg/m$^2$, administered intravenously every 84 hours; 700 mg/m$^2$, administered intravenously every 84 hours; 750 mg/m$^2$, administered intravenously every 84 hours; 800 mg/m$^2$, administered intravenously every 84 hours; 100 mg/m$^2$, administered intravenously every 96 hours; 125 mg/m$^2$, administered intravenously every 96 hours; 150 mg/m$^2$, administered intravenously every 96 hours; 200 mg/m$^2$, administered intravenously every 96 hours; 250 mg/m$^2$, administered intravenously every 96 hours; 275 mg/m$^2$, administered intravenously every 96 hours; 300 mg/m$^2$, administered intravenously every 96 hours; 350 mg/m$^2$, administered intravenously every 96 hours; 400 mg/m$^2$, administered intravenously every 96 hours; 425 mg/m$^2$, administered intravenously every 96 hours; 450 mg/m$^2$, administered intravenously every 96 hours; 500 mg/m$^2$, administered intravenously every 96 hours; 550 mg/m$^2$, administered intravenously every 96 hours; 600 mg/m$^2$, administered intravenously every 96 hours; 650 mg/m$^2$, administered intravenously every 96 hours; 700 mg/m$^2$, administered intravenously every 96 hours; 750 mg/m$^2$, administered intravenously every 96 hours; 800 mg/m$^2$, administered intravenously every 96 hours; 100 mg/m$^2$, administered orally twice weekly; 125 mg/m$^2$, administered orally twice weekly; 150 mg/m$^2$, administered orally twice weekly; 200 mg/m$^2$, administered orally twice weekly; 250 mg/m$^2$, administered orally twice weekly; 275 mg/m$^2$, administered orally twice weekly; 300 mg/m$^2$, administered orally twice weekly; 350 mg/m$^2$, administered orally twice weekly; 400 mg/m$^2$, administered orally twice weekly; 425 mg/m$^2$, administered orally twice weekly; 450 mg/m$^2$, administered orally twice weekly; 500 mg/m$^2$, administered orally twice weekly; 550 mg/m$^2$, administered orally twice weekly; 600 mg/m$^2$, administered orally twice weekly; 650 mg/m$^2$, administered orally twice weekly; 700 mg/m$^2$, administered orally twice weekly; 750 mg/m$^2$, administered orally twice weekly; 800 mg/m$^2$, administered orally twice weekly; 100 mg/m$^2$, administered orally every 72 hours; 125 mg/m$^2$, administered orally every 72 hours; 150 mg/m$^2$, administered orally every 72 hours; 200 mg/m$^2$, administered orally every 72 hours; 250 mg/m$^2$, administered orally every 72 hours; 275 mg/m$^2$, administered orally every 72 hours; 300 mg/m$^2$, administered orally every 72 hours; 350 mg/m$^2$, administered orally every 72 hours; 400 mg/m$^2$, administered orally every 72 hours; 425 mg/m$^2$, administered orally every 72 hours; 450 mg/m$^2$, administered orally every 72 hours; 500 mg/m$^2$, administered orally every 72 hours; 550 mg/m$^2$, administered orally every 72 hours; 600 mg/m$^2$, administered orally every 72 hours; 650 mg/m$^2$, administered orally every 72 hours; 700 mg/m$^2$, administered orally every 72 hours; 750 mg/m$^2$, administered orally every 72 hours; 800 mg/m$^2$, administered orally every 72 hours; 100 mg/m$^2$, administered orally every 84 hours; 125 mg/m$^2$, administered orally every 84 hours; 150 mg/m$^2$, administered orally every 84 hours; 200 mg/m$^2$, administered orally every 84 hours; 250 mg/m$^2$, administered orally every 84 hours; 275 mg/m$^2$, administered orally every 84 hours; 300 mg/m$^2$, administered orally every 84 hours; 350 mg/m$^2$, administered orally every 84 hours; 400 mg/m$^2$, administered orally every 84 hours; 425 mg/m$^2$, administered orally every 84 hours; 450 mg/m$^2$, administered orally every 84 hours; 500 mg/m$^2$, administered orally every 84 hours; 550 mg/m$^2$, administered orally every 84 hours; 600 mg/m$^2$, administered orally every 84 hours; 650 mg/m$^2$, administered orally every 84 hours; 700 mg/m$^2$, administered orally every 84 hours; 750 mg/m², administered orally every 84 hours; 800 mg/m², administered orally every 84 hours; 100 mg/m², administered orally every 96 hours; 125 mg/m², administered orally every 96 hours; 150 mg/m², administered orally every 96 hours; 200 mg/m², administered orally every 96 hours; 250 mg/m², administered orally every 96 hours; 275 mg/m², administered orally every 96 hours; 300 mg/m², administered orally every 96 hours; 350 mg/m², administered orally every 96 hours; 400 mg/m², administered orally every 96 hours; 425 mg/m², administered orally every 96 hours; 450 mg/m², administered orally every 96 hours; 500 mg/m², administered orally every 96 hours; 550 mg/m², administered orally every 96 hours; 600 mg/m², administered orally every 96 hours; 650 mg/m², administered orally every 96 hours; 700 mg/m², administered orally every 96 hours; 750 mg/m², administered orally every 96 hours; or 800 mg/m², administered orally every 96 hours.

Minimum and maximum threshold levels of a metabolite depend on a variety of factors, such as the type of subject, metabolite, therapeutic agent, and type of sample. Minimum and maximum threshold levels may be expressed in absolute terms, e.g., in units of concentration, or in relative terms, e.g., in ratios relative to a baseline or reference value. For example, the minimum threshold (below which a patient may receive a dose increase or additional dose) could also be calculated in terms of increase from a pre-treatment DHO level or baseline level.

Minimum threshold levels of DHO in a human plasma sample may be about 0 ng/ml, about 10 ng/mL, about 20 ng/mL, about 50 ng/mL, about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about 850 ng/mL, about 900 ng/mL, about 950 ng/mL, about 1000 ng/mL, about 1250 ng/ml, about 1500 ng/ml, about 1750 ng/ml, about 2000 ng/ml, about 2500 ng/ml, about 3000 ng/ml, about 3500 ng/ml, about 4000 ng/ml, about 4500 ng/ml, about 5000 ng/ml, about 6000 ng/ml, about 8000 ng/ml, about 10,000 ng/ml, about 12,000 ng/ml, about 15,000 ng/ml, about 20,000 ng/ml, about 25,000 ng/ml, about 30,000 ng/ml, about 40,000 ng/ml, about 50,000 ng/ml, about 75,000 ng/ml, about 100,000 ng/ml, about 150,000 ng/ml, about 200,000 ng/ml, about 300,000 ng/ml, or about 400,000 ng/ml. The minimum threshold may include any value that falls between the values recited above. Thus, the minimum threshold may include any value between 0 ng/ml and 400.00 ng/ml.

Maximum threshold levels of DHO in a human plasma sample may be about 50 ng/mL, about 100 ng/mL, about 150 ng/mL, about 200 ng/mL, about 250 ng/mL, about 300 ng/mL, about 350 ng/mL, about 400 ng/mL, about 450 ng/mL, about 500 ng/mL, about 550 ng/mL, about 600 ng/mL, about 650 ng/mL, about 700 ng/mL, about 750 ng/mL, about 800 ng/mL, about 850 ng/mL, about 900 ng/mL, about 950 ng/mL, about 1000 ng/mL, about 1250 ng/ml, about 1500 ng/ml, about 1750 ng/ml, about 2000 ng/ml, about 2500 ng/ml, about 3000 ng/ml, about 3500 ng/ml, about 4000 ng/ml, about 4500 ng/ml, about 5000 ng/ml, about 6000 ng/ml, about 8000 ng/ml, about 10,000 ng/ml, about 12,000 ng/ml, about 15,000 ng/ml, about 20,000 ng/ml, about 25,000 ng/ml, about 30,000 ng/ml, about 40,000 ng/ml, about 50,000 ng/ml, about 75,000 ng/ml, about 100,000 ng/ml, about 150,000 ng/ml, about 200,000 ng/ml, about 300,000 ng/ml, about 400,000 ng/ml, or about 500,000 ng/ml. The maximum threshold may include any value that falls between the values recited above. Thus, the maximum threshold may include any value between 50 ng/ml and 500.00 ng/ml.

The minimum threshold of DHO may be about 1.5 times the baseline level, about 2 times the baseline level, about 2.5 times the baseline level, about 3 times the baseline level, about 4 times the baseline level, about 5 times the baseline level, about 10 times the baseline level, about 20 times the baseline level, about 50 times the baseline level, about 100 times the baseline level, about 200 times the baseline level, about 500 times the baseline level, about 1000 times the baseline level, about 2000 times the baseline level, or about 5000 times the baseline level. The minimum threshold may include any ratio that falls between those recited above. Thus, the minimum threshold may be any ratio between 1.5 times the baseline level and 5000 times the baseline level.

The maximum threshold of DHO may be about 2 times the baseline level, about 2.5 times the baseline level, about 3 times the baseline level, about 4 times the baseline level, about 5 times the baseline level, about 10 times the baseline level, about 20 times the baseline level, about 50 times the baseline level, about 100 times the baseline level, about 200 times the baseline level, about 500 times the baseline level, about 1000 times the baseline level, about 2000 times the baseline level, about 5000 times the baseline level, or about 10,000 times the baseline level. The maximum threshold may include any ratio that falls between those recited above. Thus, the maximum threshold may be any ratio between 2 times the baseline level and 10,000 times the baseline level.

The DHODH inhibitor may be any DHODH inhibitor, such as those described below.

Dosing of the DHODH inhibitor may account for the formulation of the DHODH inhibitor. For example, DHODH inhibitors, such as brequinar, leflunomide, and teriflunomide, may be provided as prodrugs, analogs, derivatives, or salts. Any of the aforementioned chemical forms may be provided in a pharmaceutically acceptable formulation, such as a micellar formulation.

Dosage of the DHODH inhibitor also depends on factors such as the type of subject and route of administration. The dosage may fall within a range for a given type of subject and route of administration, or the dosage may adjusted by a specified amount for a given type of subject and route of administration. For example, dosage of brequinar for oral or intravenous administration to a subject, such as human or mouse, may be about 1 mg/kg, about 2 mg/kg, about 5 mg/kg, about 7.5 mg/kg, about 10 mg/kg, about 15 mg/kg, about 20 mg/kg, about 25 mg/kg, about 50 mg/kg, about 75 mg/kg, or about 100 mg/kg. Dosage of brequinar for oral or intravenous administration to a subject, such as human or mouse, may be adjusted by about 1 mg/kg, about 2 mg/kg, about 5 mg/kg, about 7.5 mg/kg, about 10 mg/kg, about 15 mg/kg, about 20 mg/kg, about 25 mg/kg, or about 50 mg/kg. Dosage of brequinar for oral or intravenous administration to an animal subject, such as a human or mouse, may be about 50 mg/m², about 100 mg/m², about 200 mg/m², about 300 mg/m², about 350 mg/m², about 400 mg/m², about 500 mg/m², about 600 mg/m², about 700 mg/m², about 800 mg/m², or about 1000 mg/m². Dosage of brequinar for oral or intravenous administration to an animal subject, such as a human or mouse, may be adjusted by about 50 mg/m², about 100 mg/m², about 200 mg/m², about 300 mg/m², about 350 mg/m², or about 400 mg/m².

FIG. 1 is a series of graphs showing levels of brequinar and DHO in three patients that have received a single dose of brequinar according to the same dosing regimen. The graph on the left is from patient #1, the graph in center is from patient #2, and the graph on the right is from patient #3. Levels of brequinar are shown in dark green, and levels of DHO are shown in red. Metabolism of brequinar is faster than average in patient #1, average in patient #2, and slower than average in patient #3. Inhibition of DHODH leads to accumulation of DHO, a substrate of DHODH. However, analysis of brequinar levels alone provides an incomplete picture of the efficacy of brequinar. Because analysis of DHO levels gives a more accurate representation of target engagement, DHO is a superior biomarker.

Figure 2:
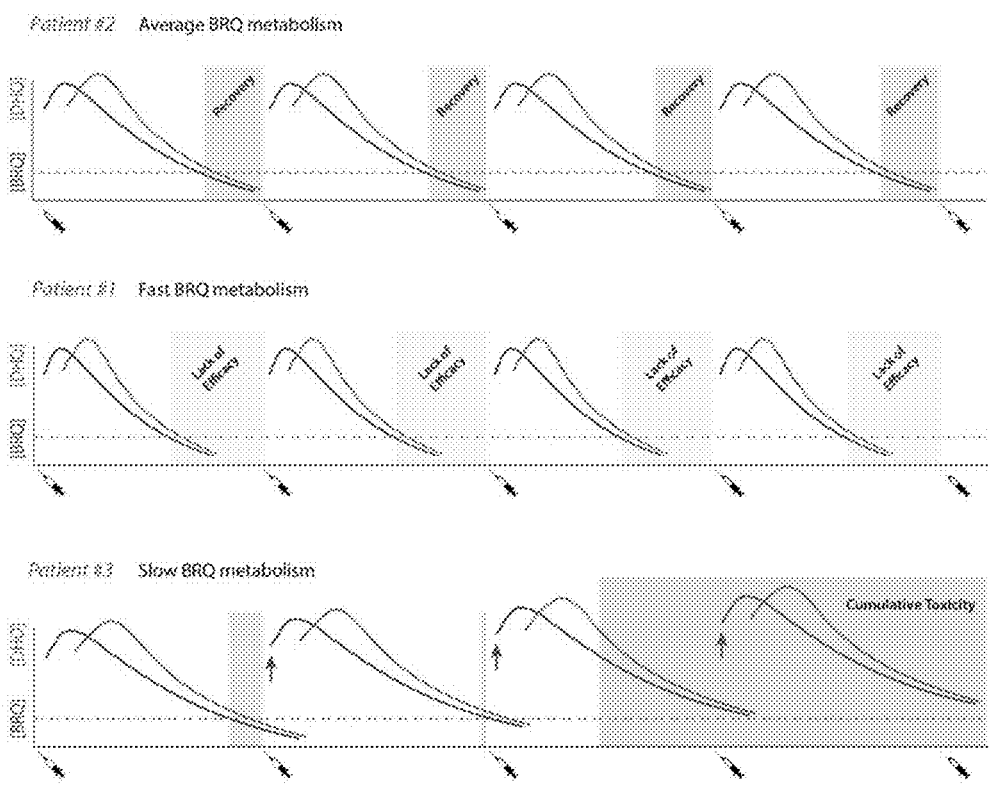
FIG. 2 is a series of graphs showing levels of brequinar and DHO in three patients that have received a multiple doses of brequinar according to the same dosing regimen.

FIG. 2 is a series of graphs showing levels of brequinar and DHO in three patients that have received a multiple doses of brequinar according to the same dosing regimen. The graph on the top is from patient #2, the graph in center is from patient #1, and the graph on the bottom is from patient #3. Levels of brequinar are shown in dark green, levels of DHO are shown in red, and the dashed line represents a threshold level above which brequinar provides sufficient inhibition of DHODH. In patient #2, i.e., a patient with an average rate of brequinar metabolism, the dosing regimen provides periods of sustained inhibition of DHODH interspersed with short recovery periods. This dosing regimen is optimal for patient #2 because the prolonged inhibition of DHODH kills leukemia cells that are sensitive to uridine starvation, while the recovery period allows an adequate supply of pyrimidines to support survival of normal cells. In patient #1, however, the duration of DHODH inhibition is not sufficient to kill leukemia cells, so this dosing regimen does not provide a therapeutic benefit. Conversely, in patient #3, the second and subsequent doses of brequinar are provided too shortly after DHODH activity is restored following the previous dose, and the pyrimidine pool is not adequately restored to support survival of normal cells. Consequently, this dosing regimen is toxic to patient #3.

Figure 3:
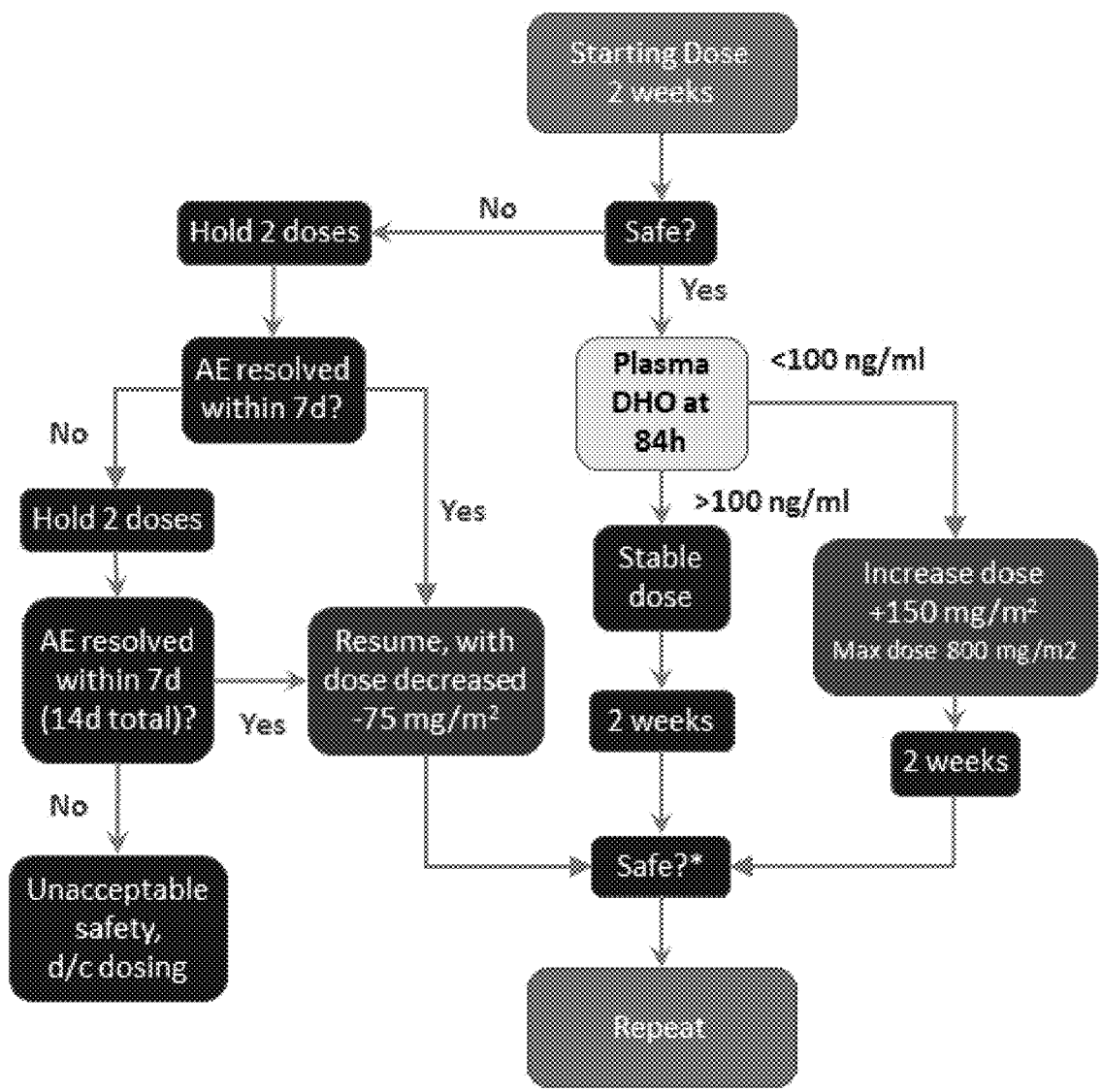
FIG. 3 is a flow chart illustrating an example of determining dose of a DHODH inhibitor for a patient according to an embodiment of the invention.

FIG. 3 is a flow chart illustrating an example of determining a dose a of DHODH inhibitor for a patient according to an embodiment of the invention. A pre-treatment DHO level is measured to determine the DHO baseline for the patient. The patient is given a starting dose for 2 weeks and examined for the presence of adverse events (AE). If adverse events occur, subsequent doses are withheld to see whether the adverse events resolve within 7 days. If adverse events resolve, dosage is decreased by 75 mg/m$^2$ and dosing is resumed. If no adverse events occur, DHO levels are analyzed at 84 hours post-administration. If DHO levels are below 100 ng/mL, dosage of brequinar is increased by 150 mg/m$^2$ but not to exceed a maximum dosage of 800 mg/m$^2$. If DHO levels are above 100 ng/mL or two times the baseline, the dosing is maintained for 2 weeks. The process can be repeated to optimize the dosing to achieve sustained elevation of DHO levels above the threshold level without adverse events.

The methods are useful for providing guidance on dosing of therapeutic agents for individuals. Therefore, the methods may be performed by any party that wishes to provide such guidance. For example and without limitation, the methods may be performed by a clinical laboratory; a physician or other medical professional; a supplier or manufacturer of a therapeutic agent; an organization that provides analytical services to a physician, clinic, hospital, or other medical service provider; or a healthcare consultant.

Disorders that can be Treated by Inhibition of DHODH

The methods of the invention are useful for determining the dosage of drugs that affect that alter the activity of DHODH to treat or prevent a disorder. The disorder may be any disease, disorder, or condition for which DHODH inhibition provides a therapeutic benefit.

For example and without limitation, one disorder that can be treated by methods of the invention is acute myeloid leukemia (AML). In AML, myeloblasts arrested in an early stage of differentiation proliferate in an uncontrolled manner and interfere with the development of other blood cells in the bone marrow. Inhibitors of dihydroorotate dehydrogenase (DHODH), an enzyme involved in pyrimidine synthesis, cause differentiation of myeloblasts and prevent their leukemia-initiating activity. The role of DHODH in AML is described in Sykes et al., Inhibition of Dihydroorotate Dehydrogenase Overcomes Differentiation Blockade in Acute Myeloid Leukemia, Cell 167, 171-186, Sep. 22, 2016; dx.doi.org/10.1016/j.cell.2016.08.057, the contents of which are incorporate herein by reference.

The use of DHODH inhibitors to treat AML requires a precise dosing regimen. Care must be taken to avoid excessive inhibition of DHODH. DHODH is an essential enzyme, and homozygous recessive mutations in DHODH cause Miller syndrome, a disorder characterized by multi-organ dysfunction. In a mouse model of AML, daily administration of high doses of the DHODH inhibitor brequinar lead to weight loss, anemia, and thrombocytopenia. At the same time, sustained exposure to brequinar is necessary to inhibit DHODH for sufficient periods to produce a therapeutic effect in the mouse AML model. Without wishing to be bound by theory, one hypothesis for the narrow therapeutic window of brequinar in treating AML in both the mouse model and in humans is that malignant cells display an increased sensitivity to DHODH inhibition. In particular, normal cells may be able to tolerate periods of nucleotide starvation that kill cancer cells due to the elevated metabolic needs of the latter.

The narrow therapeutic window of DHODH inhibition likely applies to other disorders as well. For example, brequinar was evaluated for treatment of solid tumor malignancies and found to be ineffective when administered over a 5-day period followed by a 3-week gap or once per week for three weeks followed by a 1-week gap. See Arteaga, C. L. et al. (1989) Phase I clinical and pharmacokinetic trial of Brequinar sodium (DuP 785; NSC 368390) Cancer Res. 49, 4648-4653; Burris, H. A., et al. (1998) Pharmacokinetic and phase I studies of brequinar (DUP 785; NSC 368390) in combination with cisplatin in patients with advanced malignancies, Invest. New Drugs 16, 19-27; Noe, D. A., et al. (1990) Phase I and pharmacokinetic study of brequinar sodium (NSC 368390), Cancer Res. 50, 4595-4599; Schwartsmann, G. et al. (1990) Phase I study of Brequinar sodium (NSC 368390) in patients with solid malignancies, Cancer Chemother. Pharmacol. 25, 345-351, the contents of each of which are incorporated herein by reference. However, brequinar may be effective for treatment of other cancers if the drug is administered in a manner that provides sustained DHODH inhibition.

It is understood that the aforementioned examples are provided for illustrative purposes only and that the methods of the invention can be used for treatment of any disorder or disease in which the measured level of DHO can be used to assess target engagement. The disorder may be one in which inhibiting DHODH is of therapeutic benefit. The disorder may be cancer. The cancer may include a solid tumor or hematological tumor. The cancer may be acute lymphoblastic leukemia (ALL), adult T cell leukemia/lymphoma (ATLL), bladder cancer, breast cancer, such as triple negative breast cancer (TNBC), glioma, head and neck cancer, leukemia, such as AML, lung cancer, such as small cell lung cancer and non-small cell lung cancer, lymphoma, multiple myeloma, neuroblastoma, osteosarcoma, ovarian cancer, prostate cancer, or renal cell cancer. The disorder may have a genetic mutation such as MYC amplification or PTEN loss that leads to increased dependence on the metabolic pathway, such as increased "addiction" to glutamine. The disorder may be an inflammatory or autoimmune disorder, such as arthritis, hepatitis, chronic obstructive pulmonary disease, multiple sclerosis, or tendonitis. The disorder may be a psychiatric disorder, such as anxiety, stress, obsessive-compulsive disorder, depression, panic disorder, psychosis, addiction, alcoholism, attention deficit hyperactivity, agoraphobia, schizophrenia, or social phobia. The disorder may be a neurological or pain disorder, such as epilepsy, stroke, insomnia, diskinesia, peripheral neuropathic pain, chronic nociceptive pain, phantom pain, deafferentation pain, inflammatory pain, joint pain, wound pain, post-surgical pain, or recurrent headache pain, appetite disorders, or motor activity disorders. The disorder may be a neurodegenerative disorder, such as Alzheimer's disease, Parkinson's disease, or Huntington's disease.

The disorder may include a class or subset of patients having a disease, disorder, or condition. For example, AML cases are classified based on cytological, genetic, and other criteria, and AML treatment strategies vary depending on classification. One AML classification system is provided by the World Health Organization (WHO). The WHO classification system includes subtypes of AML provided in Table 1 and is described in Falini B, et al. (October 2010) "New classification of acute myeloid leukemia and precursor-related neoplasms: changes and unsolved issues" Discov Med. 10 (53): 281-92, PMID 21034669, the contents of which are incorporated herein by reference.

TABLE 1

| Name | Description |
| --- | --- |
| Acute myeloid leukemia with recurrent genetic abnormalities | Includes:<br>AML with translocations between chromosome 8 and 21 - [t(8; 21)(q22; q22); ] RUNX1/RUNX1T1; (ICD-O 9896/3);<br>AML with inversions in chromosome 16 - [inv(16)(p13.1q22)] or internal translocations in it - [t(16; 16)(p13.1; q22); ] CBFB/MYH11; (ICD-O 9871/3);<br>Acute promyelocytic leukemia with translocations between chromosome 15 and 17 - [t(15; 17)(q22; q12); ] RARA/PML; (ICD-O 9866/3);<br>AML with translocations between chromosome 9 and 11 - [t(9; 11)(p22; q23); ] MLLT3/MLL;<br>AML with translocations between chromosome 6 and 9 - [t(6; 9)(p23; q34); ] DEK/NUP214;<br>AML with inversions in chromosome 3 - [inv(3)(q21q26.2)] or internal translocations in it - [t(3; 3)(q21; q26.2); ] RPN1/EVI1;<br>Megakaryoblastic AML with translocations between chromosome 1 and 22 - [t(1; 22)(p13; q13); ] RBM15/MKL1;<br>AML with mutated NPM1<br>AML with mutated CEBPA |
| AML with myelodys-plasia-related changes | Includes people who have had a prior documented myelodysplastic syndrome (MDS) or myeloproliferative disease (MPD) that then has transformed into AML, or who have cytogenetic abnormalities characteristic for this type of AML (with previous history of MDS or MPD that has gone unnoticed in the past, but the cytogenetics is still suggestive of MDS/MPD history). This category of AML occurs most often in elderly people and often has a worse prognosis. Includes:<br>AML with complex karyotype<br>Unbalanced abnormalities<br>AML with deletions of chromosome 7 - [del(7q); ]<br>AML with deletions of chromosome 5 - [del(5q); ] |

TABLE 1-continued

| Name | Description |
| --- | --- |
| | AML with unbalanced chromosomal aberrations in chromosome 17 - [i(17q)/t(17p); ]<br>AML with deletions of chromosome 13 - [del(13q); ]<br>AML with deletions of chromosome 11 - [del(11q); ]<br>AML with unbalanced chromosomal aberrations in chromosome 12 - [del(12p)/t(12p); ]<br>AML with deletions of chromosome 9 - [del(9q); ]<br>AML with aberrations in chromosome X - [idic(X)(q13); ]<br>Balanced abnormalities<br>AML with translocations between chromosome 11 and 16 - [t(11; 16)(q23; q13.3); ], unrelated to previous chemotherapy or ionizing radiation<br>AML with translocations between chromosome 3 and 21 - [t(3; 21)(p26.2; q22.1); ], unrelated to previous chemotherapy or ionizing radiation<br>AML with translocations between chromosome 1 and 3 - [t(1; 3)(p36.3; q21.1); ]<br>AML with translocations between chromosome 2 and 11 - [t(2; 11)(p21; q23); ], unrelated to previous chemotherapy or ionizing radiation<br>AML with translocations between chromosome 5 and 12 - [t(5; 12)(q33; q12); ]<br>AML with translocations between chromosome 5 and 7 - [t(5; 7)(q33; q11.2); ]<br>AML with translocations between chromosome 5 and 17 - [t(5; 17)(q33; p13); ]<br>AML with translocations between chromosome 5 and 10 - [t(5; 10)(q33; q21); ]<br>AML with translocations between chromosome 3 and 5 - [t(3; 5)(q25; q34); ] |
| Therapy-related myeloid neoplasms | Includes people who have had prior chemotherapy and/or radiation and subsequently develop AML or MDS. These leukemias may be characterized by specific chromosomal abnormalities, and often carry a worse prognosis. |
| Myeloid sarcoma | Includes myeloid sarcoma. |
| Myeloid proliferations related to Down syndrome | Includes so-called "transient abnormal myelopoiesis" and "Myeloid leukemia associated with Down syndrome" |
| Blastic plasmacytoid dendritic cell neoplasm | Includes so-called "blastic plasmacytoid dendritic cell neoplasm" |
| AML not otherwise categorized | Includes subtypes of AML that do not fall into the above categories<br>AML with minimal differentiation<br>AML without maturation<br>AML with maturation<br>Acute myelomonocytic leukemia<br>Acute monoblastic and monocytic leukemia<br>Acute erythroid leukemia<br>Acute megakaryoblastic leukemia<br>Acute basophilic leukemia<br>Acute panmyelosis with myelofibrosis |

An alternative classification scheme for AML is the French-American-British (FAB) classification system. The FAB classification system includes the subtypes of AML provided in Table 2 and is described in Bennett J M, et al. (August 1976). "Proposals for the classification of the acute leukaemias. French-American-British (FAB) co-operative group" Br. J. Haematol. 33 (4): 451-8, doi:10.1111/j.1365-2141.1976.tb03563.x. PMID 188440; and Bennett J M, et al. (June 1989) "Proposals for the classification of chronic (mature) B and T lymphoid leukaemias. French-American-British (FAB) Cooperative Group" J. Clin. Pathol. 42 (6): 567-84, doi:10.1136/jcp.42.6.567, PMC 1141984, PMID 2738163, the contents of each of which are incorporated herein by reference.

TABLE 2

| Type | Name | Cytogenetics |
| --- | --- | --- |
| M0 | acute myeloblastic leukemia, minimally differentiated | |
| M1 | acute myeloblastic leukemia, without maturation | |
| M2 | acute myeloblastic leukemia, with granulocytic maturation | t(8; 21)(q22; q22), t(6; 9) |
| M3 | promyelocytic, or acute promyelocytic leukemia (APL) | t(15; 17) |
| M4 | acute myelomonocytic leukemia | inv(16)(p13q22), del(16q) |
| M4eo | myelomonocytic together with bone marrow eosinophilia | inv(16), t(16; 16) |
| M5 | acute monoblastic leukemia (M5a) or acute monocytic leukemia (M5b) | del (11q), t(9; 11), t(11; 19) |
| M6 | acute erythroid leukemias, including erythroleukemia (M6a) and very rare pure erythroid leukemia (M6b) | |
| M7 | acute megakaryoblastic leukemia | t(1; 22) |

The disorder may include a sub-population of patients. For example, the patients may be pediatric, newborn, neonates, infants, children, adolescent, pre-teens, teenagers, adults, or elderly. The patients may be in critical care, intensive care, neonatal intensive care, pediatric intensive care, coronary care, cardiothoracic care, surgical intensive care, medical intensive care, long-term intensive care, an operating room, an ambulance, a field hospital, or an out-of-hospital field setting.

Providing Doses of a DHODH Inhibitor

Methods of the invention may include providing a DHODH inhibitor to a subject according to a dosing regimen or dosage determined as described above. Providing the DHODH inhibitor to the subject may include administering it to the subject. A dose may be administered as a single unit or in multiple units. The DHODH inhibitor may be administered by any suitable means. For example and without limitation, the DHODH inhibitor may be administered orally, intravenously, enterally, parenterally, dermally, buccally, topically, transdermally, by injection, intravenously, subcutaneously, nasally, pulmonarily, or with or on an implantable medical device (e.g., stent or drug-eluting stent or balloon equivalents).

In some embodiments, the methods include assessing a DHO level in a sample from a subject, and determining whether that level is within a threshold range (e.g., above a minimal threshold and/or below a potential toxicity threshold) that warrants dosing, and/or that warrants dosing at a particular level or in a particular amount.

The methods may include administering at least one dose of the DHODH inhibitor to a subject whose plasma DHO level has been determined and is below a pre-determined threshold (e.g., a pre-determined potential toxicity threshold and/or a pre-determined potential efficacy threshold). In some embodiments, the predetermined threshold reflects percent inhibition of DHODH in the subject relative to a baseline determined for the subject. In some embodiments, the baseline is determined by an assay.

For example, in some embodiments, in order to maintain inhibition of DHODH at an effective threshold, multiple doses of the DHODH inhibitor may be administered. In some embodiments, dosing of the DHODH inhibitor can occur at different times and in different amounts. The present disclosure encompasses those methods that can maintain inhibition of DHODH at a consistent level at or above the efficacy threshold throughout the course of treatment. In some embodiments, the amount of inhibition of DHODH is measured by the amount of DHO in the plasma of a subject.

In some embodiments, more than one dose of the DHODH inhibitor is administered to the subject. In some embodiments, the method further comprises a step of re-determining the subject's plasma DHO level after administration of the at least one dose. In some embodiments, the subject's plasma DHO level is re-determined after each dose. In some embodiments, the method further comprises administering at least one further dose of the DHODH inhibitor after the subject's plasma DHO level has been determined again (e.g., after administering a first or previous dose), and is below the pre-determined threshold. If the subject's plasma DHO level is determined to be above a pre-determined threshold, dosing can be discontinued. In some embodiments, therefore, no further dose of the DHODH inhibitor is administered until the subject's plasma DHO level has been determined to again be below a pre-determined threshold.

The methods may include administering a DHODH inhibitor to a subject at a dosage level at or near a cell-lethal level. Such dosage can be supplemented with a later dose at a reduced level, or by discontinuing of dosing. For example, in some embodiments, the present disclosure provides a method of administering a dihydroorotate dehydrogenase inhibitor to a subject in need thereof, the method comprising: administering a plurality of doses of a DHODH inhibitor, according to a regimen characterized by at least first and second phases, wherein the first phase involves administration of at least one bolus dose of a DHODH inhibitor at a cell-lethal level; and the second phase involves either: administration of at least one dose that is lower than the bolus dose; or absence of administration of a DHODH inhibitor.

In some embodiments, a DHODH inhibitor is not administered during a second phase. In some embodiments, a second phase involves administration of uridine rescue therapy. In some embodiments, a bolus dose is or comprises a cell lethal dose. In some embodiments, a cell lethal dose is an amount of a DHODH inhibitor that is sufficient to cause apoptosis in normal (e.g., non-cancerous) cells in addition to target cells (e.g., cancer cells).

In some embodiments, the first phase and the second phase each comprise administering a DHODH inhibitor. In some embodiments, the first phase and the second phase are at different times. In some embodiments, the first phase and the second phase are on different days. In some embodiments, the first phase lasts for a period of time that is less than four days. In some embodiments, the first phase comprises administering a DHODH inhibitor, followed by a period of time in which no DHODH inhibitor is administered. In some embodiments, the period of time in which no DHODH inhibitor is administered is 3 to 7 days after the dose during the first phase. In some embodiments, the first phase comprises administering more than one dose.

In some embodiments, a DHODH inhibitor is administered during a second phase. In some embodiments, a DHODH inhibitor is administered sub-cell-lethal levels during the second phase. In some embodiments, the first phase is repeated after the second phase. In some embodiments, both the first and second phases are repeated.

In some embodiments, the present disclosure provides a method of administering a DHODH inhibitor to a subject in need thereof, according to a multi-phase protocol comprising: a first phase in which at least one dose of the DHODH inhibitor is administered to the subject; and a second phase in which at least one dose of the DHODH inhibitor is administered to the subject, wherein one or more doses administered in the second phase differs in amount and/or timing relative to other doses in its phase as compared with the dose(s) administered in the first phase.

In some embodiments, a DHO level is determined in a sample from the subject between the first and second phases. In some embodiments, the sample is a plasma sample. In some embodiments, the timing or amount of at least one dose administered after the DHO level is determined or differs from that of at least one dose administered before the DHO level was determined.

In some embodiments, the amount of DHODH inhibitor that is administered to the patient is adjusted in view of the DHO level in the subject's plasma. For example, in some embodiments, a first dose is administered in the first phase. In some embodiments, DHO level is determined at a period of time after administration of the first dose.

In some embodiments, if the DHO level is below a pre-determined level, the amount of DHODH inhibitor administered in a second or subsequent dose is increased and/or the interval between doses is reduced. For example, in some such embodiments, the amount of DHODH inhibitor administered may be increased, for example, by 100 mg/m$^2$. In some embodiments, the amount of DHODH inhibitor administered in a second or subsequent dose is increased by 150 mg/m$^2$. In some embodiments, the amount of DHODH inhibitor administered in a second or subsequent dose is increased by 200 mg/m$^2$. In some embodiments, the amount of DHODH inhibitor administered may be increased by an adjustment amount determined based on change in DHO levels observed between prior doses of different amounts administered to the subject.

In some embodiments, if the DHO level is above a pre-determined level, the amount of DHODH inhibitor administered in a second or subsequent dose is the same as the amount administered in the first or previous dose and/or the interval between doses is the same.

In some embodiments, if the DHO level is above a pre-determined level, the amount of DHODH inhibitor in a second or subsequent dose is decreased and/or the interval between doses is increased. For example, in some such embodiments, the amount of DHODH inhibitor administered may be decreased, for example, by 50 mg/m$^2$. In some embodiments, if the DHO level is above a pre-determined level, the amount of DHODH inhibitor in a second or subsequent dose is decreased by 75 mg/m$^2$. In some embodiments, if the DHO level is above a pre-determined level, the amount of DHODH inhibitor in a second or subsequent dose is decreased by 100 mg/m$^2$. In some embodiments, the amount of DHODH inhibitor administered may be decreased by an adjustment amount determined based on change in DHO levels observed between prior doses of different amounts administered to the subject.

In some embodiments, the present disclosure provides a method of administering a later dose of a DHODH inhibitor to a patient who has previously received an earlier dose of the DHODH inhibitor, wherein the patient has had a level of DHO assessed subsequent to administration of the earlier dose, and wherein the later dose is different than the earlier dose. The later dose may be different from the earlier dose in amount of DHODH inhibitor included in the dose, time interval relative to an immediately prior or immediately subsequent dose, or combinations thereof. The amount of DHODH inhibitor in the later dose may be less than that in the earlier dose.

The method may include administering multiple dose of the DHODH inhibitor, separated from one another by a time period that is longer than 2 days and shorter than 8 days for example, the time period may be about 3 days.

In some embodiments, the DHO level is determined in a sample from the subject before each dose is administered, and dosing is delayed or skipped if the determined DHO level is above a pre-determined threshold. For example, the DHO level may be determined about 12 hours, about 24 hours, about 36 hours, about 48 hours, about 60 hours, about 72 hours, about 84 hours, or about 96 hours after administration of a DHODH inhibitor The method may include administering the DHODH inhibitor according to a regimen approved in a trial in which a level of DHO was measured in a patients between doses of the DHODH inhibitor. The regimen may include multiple doses whose amount and timing were determined in the trial to maintain the DHO level within a range determined to indicate a degree of DHODH inhibition below a toxic threshold and above a minimum threshold. The regimen may include determining the DHO level in the subject after administration of one or more doses of the DHODH inhibitor.

In some embodiments, the regimen includes a dosing cycle in which an established pattern of doses is administered over a first period of time. In some embodiments, the regimen comprises a plurality of the dosing cycles. In some embodiments, the regimen includes a rest period during which the DHODH inhibitor is not administered between the cycles.

Compositions Containing DHODH Inhibitors

The compositions of the invention include DHODH inhibitors. Several DHODH inhibitors are known in the art. For example, inhibitors of DHODH include brequinar, leflunomide, and teriflunomide. Brequinar, which has the systematic name 6-fluoro-2-(2'-fluoro-1,1' biphenyl-4-yl)-3-methyl-4-quinoline carboxylic acid, has the following structure:

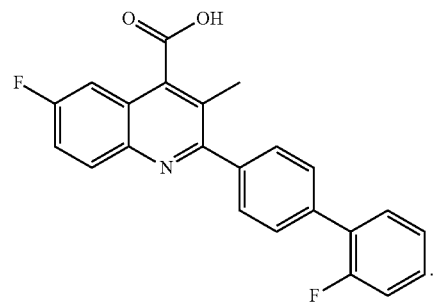 [SMILES: Cc1c(-c2ccc(-c3ccccc3F)cc2)nc2ccc(F)cc2c1C(=O)O ; "."]

Brequinar and related compounds are described in, for example, U.S. Pat. Nos. 4,680,299 and 5,523,408, the contents of which are incorporated herein by reference. The use of brequinar to treat leukemia is described in, for example, U.S. Pat. No. 5,032,597 and WO 2017/037022, the contents of which are incorporated herein by reference. Leflunomide, N-(4'-trifluoromethylphenyl)-5-methylisoxazole-4-carboxamide (I), is described in, for example, U.S. Pat. No. 4,284,786, the contents of which are incorporated herein by reference. Teriflunomide, 2-cyano-3-hydroxy-N-[4-(trifluoromethyl)phenyl]-2-butenamide, is described in, for example, U.S. Pat. No. 5,679,709, the contents of which are incorporated herein by reference.

The DHODH inhibitor may be provided as a prodrug, analog, derivative, or salt. The DHODH inhibitor may be provided in a micellar formulation.

The DHODH inhibitors, including prodrugs, analogs, derivatives, and salts thereof, may be provided as pharmaceutical compositions. A pharmaceutical composition may be in a form suitable for oral use, for example, as tablets, troches, lozenges, fast-melts, aqueous or oily suspensions, dispersible powders or granules, emulsions, hard or soft capsules, syrups or elixirs. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the compounds in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc.

The tablets may be uncoated, or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874, to form osmotic therapeutic tablets for control release. Preparation and administration of compounds is discussed in U.S. Pat. No. 6,214,841 and U.S. Pub. No. 2003/0232877, the contents of each of which are incorporated by reference herein.

Formulations for oral use may also be presented as hard gelatin capsules in which the compounds are mixed with an inert solid diluent, for example calcium carbonate, calcium phosphate or kaolin, or as soft gelatin capsules in which the compounds are mixed with water or an oil medium, for example peanut oil, liquid paraffin or olive oil.

An alternative oral formulation, where control of gastrointestinal tract hydrolysis of the compound is sought, can be achieved using a controlled-release formulation, where a compound of the invention is encapsulated in an enteric coating.

Aqueous suspensions may contain the compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally occurring phosphatide, for example lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the compounds in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compounds in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, such as glycerol, propylene glycol, sorbitol or sucrose. Such formulations may also contain a demulcent, a preservative, and agents for flavoring and/or coloring. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Pharmaceutical compositions may include other pharmaceutically acceptable carriers, such as sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin (glycerol), erythritol, xylitol. sorbitol, mannitol and polyethylene glycol; esters, such asethyl oleate and ethyllaurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. The pharmaceutically acceptable carrier may be an encapsulation coating. For example, the encapsulation coating may contain carrageenan, cellulose acetate phthalate, cellulose acetate succinate, cellulose acetate trimellitate, collagen, gelatin, hydroxypropyl methyl cellulose acetate, a methyl acrylate-methacrylic acid copolymer, polyvinyl acetate phthalate shellac, sodium alginate, starch, or zein.

The N-acylethanolamide compounds, including prodrugs, analogs, and derivatives thereof, may be provided as pharmaceutically acceptable salts, such as nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphor sulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Other pharmaceutically acceptable salts may be found in, for example, Remington, The Science and Practice of Pharmacy (20th ed. 2000). Representative alkali or alkaline earth metal salts include sodium, lithium, potassium, calcium, magnesium, and the like. In some embodiments, a pharmaceutically acceptable salt is an alkali salt. In some embodiments, a pharmaceutically acceptable salt is a sodium salt. In some embodiments, a pharmaceutically acceptable salt is an alkaline earth metal salt. In some embodiments, pharmaceutically acceptable salts include, when appropriate, nontoxic ammonium, quaternary ammonium, and amine cations formed using counter ions such as halide, hydroxide, carboxylate, sulfate, phosphate, nitrate, alkyl having from 1 to 6 carbon atoms, sulfonate and aryl sulfonate.

Synthesis of Brequinar and Related Compounds

The invention provides methods of making a 2-(2'-halo-1-1'-biphenyl-4-yl)-quinoline carboxylic acid, such as brequinar. The methods include incubating a compound of formula (I) with a compound of formula (II) in a mixture containing a base and adding an acid to the mixture, thereby creating a compound of formula (III) according to following reaction:

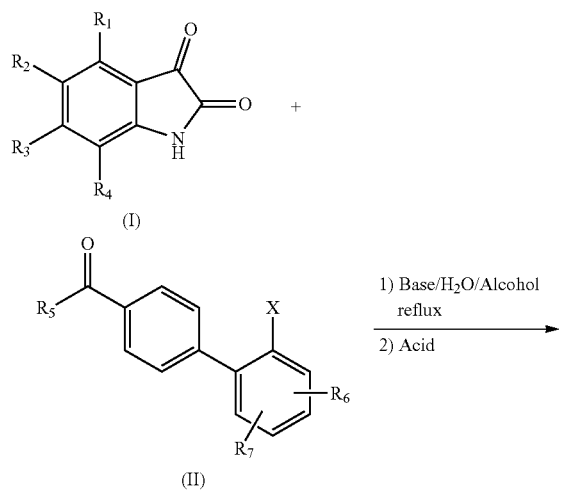

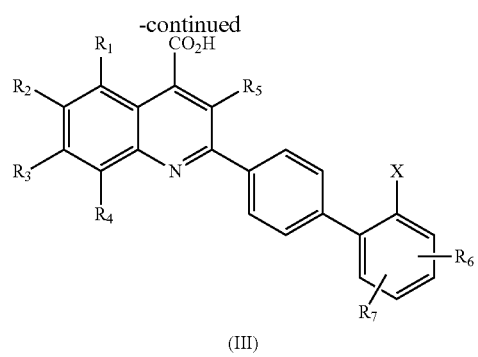

in which:

$R_1$, $R_2$, $R_3$, and $R_4$ are independently H, F, Cl, Br, I, $CH_3$, $CF_3$, $SCH_3$ or $CH_2CH_3$, at least two of $R_1$, $R^2$, $R_3$, and $R_4$ being H;

$R_5$ is H, alkoxy of 1-3 carbon atoms, or alkyl of 1-2 carbon atoms;

$R_6$ and $R_7$ are independently H, F, Cl, Br, alkyl of 1-5 carbon atoms, $NO_2$, OH, $CF_3$ or $OCH_3$;

X is a halogen; and the incubating step includes at least one of:
incubating the mixture at a temperature of from about 60° C. to about 70° C., the mixture containing a molar ratio of the base to the compound of formula (II) of from about 5:1 to about 8:1, and incubating the mixture for from about 15 hours to about 30 hours.

An insight of the invention is that optimizing the conditions of the first step, i.e., incubating compounds of formula (I) and formula (II) in the presence of a base, improves yield of the product. One key variable is the molar ratio of the base to the compound of formula (II). Higher yields are achieved with when this molar ratio is optimized. For example, the molar ratio of the base to the compound of formula (II) may be from about 5:1 to about 8:1, from about 6.5:1 to about 7.5:1, or about 7:1.

Any suitable base may be used. Preferably, the base is KOH, NaOH, and $NH_4OH$.

Any suitable alcohol may be used. For example, the alcohol may be methanol, ethanol, 1-propanol, 2-propanol, butanol, 2-methyl-1-propanol, or pentanol.

Another important variable in the incubation step is the temperature. A minimum temperature is required for the reaction to occur, but temperatures that are too high result in increased generation of undesired side products. Thus, the temperature may be from about 60° C. to about 70° C., from about 60° C. to about 65° C., or about 60° C.

Another important variable in the incubation step is the duration. A minimum time is required for the reaction to occur, but excessive incubation time results in the generation of undesired side products. Thus, the length of incubation may be from about 15 hours to about 30 hours, from about 15 hours to about 25 hours, or from about 15 hours to about 20 hours.

The reaction outlined above can be performed using one or more of an optimized molar ratio of the base to the compound of formula (II) as described above, an optimized temperature as described above, and an optimized incubation time as described above. Thus, the reaction may include one, two, or three of the optimized variables described above.

For the acid addition step, the acid may be any suitable acid. For example, the acid may be HCl or acetic acid.

The method may provide a minimum yield of the compound of formula (III). For example, the yield of the compound of formula (III) may be at least 70%, at least 75%, at least 80%, at least 85%, at least 90%, or at least 95%.

The compound of formula (III) may be brequinar. The compound of formula (III) may have the structure represented by formula (IV):

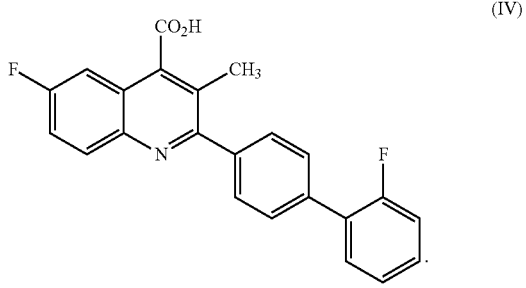 [SMILES: Cc1c(-c2ccc(-c3ccccc3F)cc2)nc2ccc(F)cc2c1C(=O)O ; "."]

(IV)

Assessing Tumor Properties

The invention also provides methods for assessing the effects of DHODH inhibitors on tumors in vivo in real time. This information obtained from such in vivo analysis may be used to determine or make adjustments to dosing regimens.

One modality for assessing the effect of an agent on a tumor is to monitor within the tumor the flux of a metabolite through a pathway whose activity is altered by the agent, such as the pathways and agents described above. Activity of metabolic pathways in vivo can be analyzed in real-time by hyperpolarization magnetic resonance imaging, as described in, for example, Miloushev, V Z et al., Hyperpolarization MRI: Preclinical Models and Potential Applications in Neuroradiology, Top Magn Reson Imaging 2016 February; 25(1): 31-37, doi: 10.1097/RMR.0000000000000076, PMID: 26848559; Di Gialleonardo, D, et al., The Potential of Metabolic Imaging, Semin Nucl Med. 2016 January; 46(1): 28-39, doi: 10.1053/j.semnuclmed.2015.09.004, PMID: 26687855; and Cho, et al., Noninvasive Interrogation of Cancer Metabolism with Hyperpolarized $^{13}$C MRI J Nucl Med 2017; 58:1201-1206, DOI: 10.2967/jnumed.116.182170, the contents of each of which are incorporated herein by reference.

Briefly, the methods entail injection of an isotopically-labeled metabolite, which can be imaged by magnetic resonance, into a subject and tracking movement of the isotope through the body. The metabolite may be a carbon-containing molecule, such as an intermediate in the pyrimidine synthesis pathway, that is enriched for an isotope of carbon, such as $^{13}$C, or nitrogen, such as $^{15}$N. The therapeutic agent may be an agent that inhibits an enzyme in a pathway through which the metabolite passes. Analysis may include comparison of metabolism of the labeled metabolite when the subject has been provided the therapeutic agent with metabolism in an untreated subject, either the same subject or a different subject having similar characteristics. The methods are useful for analysis of tumors due to the increase flux through certain metabolic pathways, such as the pyrimidine synthesis pathway, in tumor cells. For example, a subject having a tumor may with increased glutamine flux (determined by isotopically-labeled glutamine) be given a DHODH inhibitor, e.g., brequinar, and isotopically-labeled DHO. If the level DHODH inhibition is high, accumulation of the metabolite can be detected at the site of the tumor.

Another way to assess the effect of an agent on a tumor in vivo in real time is to analyze oxygenation of the tumor. Many solid tumors contain regions of poor oxygenation due to the inability of the vasculature to keep pace with the rapid growth of tumor cells. To continue to proliferating when the blood supply is inadequate, tumor cells often alter their metabolism to derive more energy from glucose metabolism and become less dependent on oxygen. Methods of measuring oxygenation levels of tissue that contains tumors is known in the art and described in, for example, Zhao, D., et al., Measuring changes in tumor oxygenation, Methods Enzymol. 2004; 386:378-418, doi.org/10.1016/S0076-6879(04)86018-X; and H Rundqvist and R S Johnson, Tumour oxygenation: implications for breast cancer prognosis, Intern Med 2013; 274: 105-112, doi: 10.1111/joim.12091, the contents of each of which are incorporated herein by reference. In some embodiments, tumor oxygenation may be measured by electron paramagnetic resonance imaging (EPR). EPR is known in the art and described in, for example, Abramović Z., et al., (eds) 11th Mediterranean Conference on Medical and Biomedical Engineering and Computing 2007. IFMBE Proceedings, vol 16. Springer, Berlin, Heidelberg, doi.org/10.1007/978-3-540-73044-6_116, ISBN 978-3-540-73043-9; and Matsumoto, et al., Low-field paramagnetic resonance imaging of tumor oxygenation and glycolytic activity in mice, J. Clin. Invest. 118:1965-1973 (2008) doi:10.1172/JCI34928, the contents of each of which are incorporated herein by reference.

A Device to Rapidly Assess Metabolite Levels

The invention also includes a device or assay to rapidly measure levels of a metabolite of interest, for e.g., DHO. Plasma from a patient is run on the assay with the objective to determine the level of metabolite in the plasma. In the described assay, set levels of the target enzyme are added with known activity. The assay quantifies the amount of metabolite present in plasma by colorimetric changes, a competitive assay, or other techniques known in the field. In one embodiment, the objective is to quantify the amount of DHO after a dose of brequinar. A patient plasma specimen is collected. The plasma is run on the assay containing set amount of DHODH. Patient DHO may compete with colored DHO in the assay and cause a change in color that can be read out as a measure of DHO level in the plasma. In another embodiment, substrate and DHODH could be lyophilized in a blood collection tube. Blood drawn into the tube could provide a visible change in color to determine if DHO is below, at or above a specified threshold. This would enable point of care monitoring of metabolite levels for rapid adjustments in dose as needed.

Devices for Notification

The invention also includes device for notifying a subject concerning a dosing regimen, such as a dosage of a DHODH inhibitor, timing for administration of a dose, timing for collection of a metabolite to determine dose adjustments, or any combination thereof, or an adjustment to a dosing regimen. The devices include a processor coupled to a memory unit. The memory unit drives the processor to receive data about a dose of a DHODH inhibitor, collect data from laboratory or point of care analysis of the metabolite tested, generate a notification about a dosing regimen or a change to the dosing regimen, and output the reminder to the subject.

The data received by the processor may contain any information related to a dose of an DHODH inhibitor provided to a subject. For example, the data may include information about the DHODH inhibitor, such as the name of the DHODH inhibitor, a classification the DHODH inhibitor, the dose or amount of the DHODH inhibitor provided to the subject, the concentration, the formulation, and the like. The data may include the route of administration, such as oral or intravenous administration. The data may include the when the dose was administered to the subject, including the day, date, hour, minute, second, time zone, or any other temporal component. The data may include information concerning multiple doses of the DHODH inhibitor that were administered to the subject. The data may include information concerning multiple agents that were administered to the subject. The data may include a metabolite level and whether a specified threshold has been reached.

The notification may include any type of reminder to the subject concerning the dosing regimen or adjustments thereto. For example, the notification may include a time for administration of the next dose of the DHODH inhibitor, the dosage of the next dose of the DHODH inhibitor, or a combination of the two. The notification may include adjustments to any of the aforementioned parameters. The notification may include information provided in absolute terms or relative terms. For example, the notification may include a time component that indicate that the next dose should be provided at a certain number of hours, e.g., 72 hours, following the previous dose, or it may indicate an objective time and/or date for administration of the next dose. The notification may indicate that the dosage should be adjusted by a defined amount, e.g., increased by 75 ng/mL, by a relative amount, e.g., increased by 50%. The dosing regimen or adjustment to the dosing regimen is based on a measured level of DHO in a sample obtained from the subject, as described above. The notification may also recommend the time for an additional blood collection for metabolite analysis based on a trend analysis of historic drug and metabolite levels, a change in disease, or new evidence for an alternative blood sampling schedule. The device may provide the notification in any manner that can be perceived by the subject. For example, output of the notification may include an audible signal, a visual signal, a tactile signal, a vibration, or any combination thereof.

The device may output the notification to a component of the device, such as a display, or it may output the notification to a remote device. The device may output the notification to a third party, such as health care professional, e.g., a physician, nurse, or other practitioner.

The memory unit may enable the processor to perform additional processes. For example, the processor may determine a dosing regimen or an adjustment to a dosing regimen, as described above.

The processor may use information stored in the memory unit to determine whether the subject has developed or is developing resistance to a DHODH inhibitor. Resistance of a subject to a DHODH inhibitor can become manifest when the interval between time points of dose administration to achieve the same effect, e.g., level of DHO, become smaller over the course of therapy, i.e., when the subject requires more frequent doses. Resistance of a subject to a DHODH inhibitor can become manifest when higher dosages are required to achieve the same effect, e.g., level of DHO, over the course of therapy. Thus, the processor may determine that intervals between time points for administration of the DHODH inhibitor have changed, e.g., grown smaller or larger, over the course of therapy, that dosages have changed, e.g., increased or decreased, over the course of therapy, or a combination of the two.

The processor may output a recommended adjustment in the dosing regimen to the subject. The recommended adjustment may include administration of a second or additional DHODH inhibitor.

The device may be, or be a part of, a portable or wearable electronic device, such as a phone, watch, belt, armband, legband, article of clothing, handheld device, or the like.

Synthetic Lethality

Methods of the invention include determining a dosing regimen that includes providing an agent that alters activity of a metabolic pathway in a tumor that is specifically dependent on that metabolic pathway. For example, tumor cells bearing a mutation that affects the activity of a first pathway may rely more heavily on the activity of a second pathway that compensates for or counteracts the altered activity of the first pathway. A change in the activity of the second pathway that may therefore be deadly to tumor cells but not to normal cells, a phenomenon called synthetic lethality. Examples of tumors with altered pathways for which a DHODH inhibitor, such as brequinar, may be synthetically lethal include tumors that have phosphatase and tensin homolog (PTEN) low, Myc protein family member amplification, a Notch protein family member mutations, and activating mutations of Ras protein family members.

Combination Therapies for Autoimmune Toxicity

Methods of the invention include determining a dosing regimen that includes providing a DHODH inhibitor, as described above, in combination with one or more other therapeutic agents. The methods may also include providing both therapeutic agents in such combination dosing regimens.

Methods of the invention include determining a dosing regimen that includes providing an agent that alters activity of a metabolic pathway, as described above, in combination with one or more other therapeutic agents. The methods may also include providing both therapeutic agents in such combination dosing regimens.

Combination therapies are useful, for example, for treating autoimmune toxicity and cytokine-associated toxicity. Autoimmune toxicity may result from an antigen-specific attack on host tissues when the targeted tumor associated antigen is expressed on nonmalignant tissue. It may result due to increased immune activation due to immune-oncology (TO) therapy. It may preferentially affect patients with pre-existing autoimmune disease such as rheumatoid arthritis, inflammatory bowel disease, and psoriasis.

Cytokine Release Syndrome (CRS)

Cytokine associated toxicity, also referred to as cytokine release syndrome (CRS) or cytokine storm, is a non-antigen specific toxicity that occurs as a result of high level immune activation. The degree of immune activation necessary to obtain clinical benefit using IO typically exceeds the level of immune activation that occurs during natural immune activation. As IO therapies have increased in potency and efficacy, CRS is increasingly recognized as a problem requiring a solution.

CRS is clinically observed in cases where large numbers of lymphocytes (B cells, T cells, and/or natural killer cells) and/or myeloid cells (macrophages, dendritic cells, and monocytes) become activated and release inflammatory cytokines including IL-1beta, TNFalpha, IFNbeta, IFNgamma, IL-6, and IL-8. CRS is caused by a hyperactivated T-cell response which is not tissue specific and thus causes reactivity with normal issue. This results in the production of high levels of CD4 T-helper cell cytokines or increased migration of cytolytic CD8 T cells within normal tissues. Weber, J. S., et al., "Toxicities of Immunotherapy for the Practitioner," Journal of Clinical Oncology, 33, no. 18 (June 2015) 2092-2099. The onset of symptoms may occur within a period of minutes to hours after administration of an IO therapy. Timing of symptom onset and CRS severity may depend on the inducing agent and the magnitude of the resulting immune cell activation. CRS can lead to serious organ damage and failure; such injury includes pulmonary infiltrates, lung injury, acute respiratory distress syndrome, cardiac dysfunction, cardiovascular shock, neurologic toxicity, disseminated intravascular coagulation (DIC), hepatic failure, or renal failure.

CRS has been reported following the administration of IO therapies including HSCT, cancer vaccines (either alone or in combination with adoptive T-cell therapy), mAbs, and CAR-T cells. CRS is a potentially life-threatening toxicity, with some patients requiring extensive intervention and life support. Patients have experienced neurological damage and/or death. Diagnosis and management of CRS in response to immune cell-based therapies is routinely based on clinical parameters and symptoms. Lee et al. has described a revised CRS grading system, shown below in Table 3. Lee, D. et al. (2014) Blood 124(2): 188-195.

TABLE 3

| Grade | Toxicity |
|---|---|
| Grade 1 | Symptoms are not life threatening and require symptomatic treatment only, e.g., fever, nausea, fatigue, headache, myalgias, malaise |
| Grade 2 | Symptoms require and respond to moderate intervention Oxygen requirement <40% or Hypotension responsive to fluids or low dose of one vasopressor or Grade 2 organ toxicity |
| Grade 3 | Symptoms require and respond to aggressive intervention Oxygen requirement ≥40% or Hypotension requiring high dose or multiple vasopressors or Grade 3 organ toxicity or grade 4 transaminitis |
| Grade 4 | Life-threatening symptoms Requirement for ventilator support or Grade 4 organ toxicity (excluding transaminitis) |
| Grade 5 | Death |

Grades 2-4 refer to CTCA.E v4.0 grading

Standard treatment involves vigilant supportive care and treatment with immunosuppressive drugs (e.g., anti-cytokine antibodies such as tocilizumab and corticosteroids). Management of CRS must be balanced with ensuring the efficacy of TO treatments. While early and/or aggressive immunosuppression may mitigate CRS, it may also limit the efficacy of the therapy. There have been reports that CRS may actually be necessary for effective treatment. The goal of CRS management is not to completely suppress it, but to prevent life-threatening toxicity while maximizing any anti-tumor effects. Lee, D. et al. (2014) Blood 124(2): 188-195.

Immuno-Oncology Therapy

The present disclosure relates particularly to methods of improving the safety of immuno-oncology (TO) treatments while maintaining efficacy. Cancer or autoimmune disease may be viewed as the result of a dysfunction of the normal immune system. The goal of TO is to utilize a patient's own immune system to effect treatment of a disorder. TO treatments may include hematopoietic stem cell transplantation (HSCT), cancer vaccines, monoclonal antibodies (mAbs), and adoptive T-cell immunotherapy Examples of Combination Therapies Compositions of the invention may include a DHODH inhibitor in combination with one or more other therapeutic agents. Examples of therapeutic agents that can be used in combination dosing regimens are described below.

Agents that Target Metabolic Pathways

The second or additional therapeutic agent may target a metabolic pathway different from the pyrimidine synthesis pathway. For example, the second agent may inhibit a glutaminase, the PI3K pathway, or orotidine 5'-monophosphate (OMP) decarboxylase.

CAR T-Cell Therapy

Adoptive T-cell immunotherapy may be performed with either natural T-cells or with engineered T-cells. Engineered T-cells can include T-cells which have been engineered to express chimeric antigen receptors (CARs) on their surface (CAR-T cells).

Autologous adoptive cell transfer involves the collection, modification, and return of a patient's immune cells, offering a promising immunotherapeutic approach for the treatment of different types of cancers. Typically, leukocytes are isolated, usually by well-established density barrier centrifugation, and T lymphocytes are expanded ex vivo using cell culture methods, often relying on the immunomodulatory action of interleukin-2. Once expanded, the cells are administered intravenously to the patent in an activated state. Such cells are referred to as effector T cells. In addition, a combination of anti-CD3 and anti-CD28 antibodies may be used as a surrogate for antigen presentation with appropriate co¬ stimulation cues to promote the proliferation of T cells in culture.

For T cells, engagement of the CD4+ and CD8+ T cell receptor (TCR) alone is not sufficient to induce persistent activation of resting naive or memory T cells. Fully functional, productive T cell activation requires a second co-stimulatory signal from a competent antigen-presenting cell (APC).

Co-stimulation is achieved naturally by the interaction of CD28, a co-stimulatory cell surface receptor on T cells, with a counter-receptor on the surface of the APC, e.g., CD80 and/or CD86. An APC may also be used for the antigen-dependent activation of T cells. To induce functional activation rather than toleragenic T cells, APCs must also express on their surface a co-stimulatory molecule. Such APCs are capable of stimulating T cell proliferation, inducing cytokine production, and acting as targets for cytolytic T lymphocytes (CTL) upon direct interaction with the T cell.

Recently, T cells have been genetically engineered to produce artificial T cell receptors on their surface called chimeric antigen receptors (CARs). CARs allow T cells to recognize a specific, pre-selected protein, or antigen, found on targeted tumor cells. CAR-T cells can be cultured and expanded in the laboratory, then re-infused to patients in a similar manner to that described above for adoptive transfer of native T cells. The CAR directs the CAR T-cell to a target cell expressing an antigen to which the CAR is specific. The CAR T cell binds the target and through operation of a stimulatory domain activates the CAR T-cell. In some embodiments, the stimulatory domain is selected from CD28, OX40, CD27, CD2, CD5, ICAM-1, LFA-1 (CD11a/CD18), 4-1BB, or a combination thereof.

CARs may be specific for any tumor antigen. In some embodiments, a CAR comprises an extracellular binding domain specific for a tumor antigen. In some embodiments, a tumor antigen is selected from TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-1 receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, ACK97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6,E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

In some embodiments, a CAR comprises an extracellular binding domain specific for a tumor targeting antibody. In some embodiments, an extracellular binding domain specific for a tumor targeting antibody binds an Fc portion of a tumor targeting antibody. In some embodiments, an extracellular binding domain specific for a tumor targeting antibody comprises an Fc receptor or an Fc binding portion thereof. In some embodiments, an Fc receptor is an Fc-gamma receptor, an Fc-alpha receptor, or an Fc epsilon receptor. In some embodiments, an extracellular binding domain can be an extracellular ligand-binding domain of CD16 (e g., CD16A or CD16B), CD32 (e g., CD32A, or CD32B), or CD64 (e g., CD64A, CD64B, or CD64C).

In some embodiments, a CAR comprises a transmembrane domain. In some embodiments, a transmembrane domain is selected from CD8α, CD8β, 4-1BB, CD28, CD34, CD4, FcεRIγ, CD16 (e g., CD16A or CD16B), OX40, CD3ζ CD3ε, CD3γ, CD3δ, TCRα, CD32 (e g., CD32A or CD32B), CD64 (e g., CD64A, CD64B, or CD64C), VEGFR2, FAS, and FGFR2B, or a combination thereof. In some embodiments, the transmembrane domain is not CD8α. In some embodiments, a transmembrane domain is a non-naturally occurring hydrophobic protein segment.

In some embodiments, a CAR comprises a co-stimulatory domain for T-cell activation. In some embodiments, a co-stimulatory domain is selected from CD28, OX40, CD27, CD2, CD5, ICAM-1, LFA-1 (CD11a/CD18), 4-1BB, GITR, HVEM, TIM1, LFA1, or CD2, a functional fragment thereof, or a combination thereof. In some embodiments, a CAR comprises two or more co-stimulatory domains. In some embodiments, the two or more co-stimulatory domains are selected from CD28, OX40, CD27, CD2, CD5, ICAM-1, LFA-1 (CD11a/CD18), 4-1BB, GITR, HVEM, TIM1, LFA1, or CD2.

Cytokine release syndrome (CRS) is a common and potentially lethal complication of CAR-T cell therapy. It is a non-antigen specific toxicity that can occur as a result of the high-levels of CAR-T cell expansion and immune activation typically required to mediate clinical benefit using modern immunotherapies such as CAR-T cell transfer. Timing of symptom onset and CRS severity depends on the inducing agent and the magnitude of immune cell activation. Symptom onset typically occurs days to occasionally weeks after T cell infusion, coinciding with maximal in vivo T-cell expansion.

The incidence and severity of CRS following CAR-T therapy for cancer has recently been reported to be greater in patients having large tumor burdens. Without wishing to be bound by any theory, it is believe that this is due to the expression of production of pro-inflammatory cytokines such as TNF-α by the adoptively transferred expanding and activated CAR-T cell populations. CRS following CAR-T therapy has been consistently associated with elevated IFNγ, IL-6, and TNF-α levels, and increases in IL-2, granulocyte macrophage-colony-stimulating factor (GM-CSF), IL-10, IL-8, IL-5, and fracktalkine have also been reported.

Cancer Vaccines

In some embodiments an immune-oncology therapy is a cancer vaccine. A cancer vaccine is an immunogenic composition which stimulates a patient's immune system to produce anti tumor antibodies, thereby enabling the immune system to target and destroy cancerous cells. In some embodiments, a cancer vaccine is a peptide vaccine. In some embodiments, a cancer vaccine is a conjugate vaccine.

In some embodiments, a cancer vaccine is used in combination with adoptive T cell therapy. In some embodiments, a cancer vaccine is administered to a patient, after which tumor specific T cells are obtained from the patient, isolated, expanded ex vivo, and then administered to the patient. In some embodiments, the ex vivo expansion of tumor specific T cells provides for a method of obtaining a greater number of T cells which may attack and kill cancerous cells than what could be obtained by vaccination alone. In some embodiments, adoptive T cell therapy comprises culturing tumor infiltrating lymphocytes. In some embodiments, one particular T cell or clone is isolated and expanded ex vivo prior to administration to a patient. In some embodiments, a T cell is obtained from a patient who has received a cancer vaccine.

Administration of cancer vaccines, either alone or in combination with adoptive T cell transfer has been reported to result in CRS.

Human Stem Cell Transplantation (HSCT)

HSCT is the transplantation of stem cells to reestablish hematopoietic function in a patient with defective bone marrow or immune system. In some embodiments, the stem cells are autologous. In some embodiments, the stem cells are allogeneic. In some embodiments the transplant is performed by intravenous infusion.

In some embodiments, autologous HSCT may be used to treat multiple myeloma, non-Hodgkin lymphoma, Hodgkin disease, acute myeloid leukemia, neuroblastoma, germ cell tumors, autoimmune disorders (e.g., systemic lupus erythematosus [SLE], systemic sclerosis), or amyloidosis.

In some embodiments, allogeneic HSCT may be used to treat acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin lymphoma, Hodgkin disease, aplastic anemia, pure red-cell aplasia, paroxysmal nocturnal hemoglobinuria, Fanconi anemia, thalassemia major, sickle cell anemia, severe combined immunodeficiency (SCID), Wiskott-Aldrich syndrome, hemophagocytic lymphohistiocytosis, inborn errors of metabolism, Epidermolysis Bullosa, severe congenital neutropenia, Shwachman-Diamond syndrome, Diamond-Blackfan anemia, or leukocyte adhesion deficiency.

In some embodiments, stem cells are obtained from a donor for administration to a patient. In some embodiments, the donor is an identical twin of the patient. In some embodiments, the donor is a matched donor related to the patient. In some embodiments, the donor is a matched donor unrelated to the patient. In some embodiments, the donor is a mismatched donor related to the patient. In some embodiments, the donor is haploidentical to the patient.

In some embodiments stem cells are obtained from bone marrow, peripheral blood, or umbilical cord blood.

HSCT may result in graft vs. host disease (GvHD), which remains a major cause of morbidity and mortality in patients undergoing HSCT. Even though there have been advances in prevention and post-transplant immunosuppressive strategies, it is estimated that 20-50% of all HSCT patients will experience at least moderate GvHD. Inflammatory cytokine release, e.g., CRS, is likely the primary mediator of acute GvHD, and activation of T-cells is one step in this complex process. Ball, L. M. & Egeler, R. M., "Acute GvHD: pathogenesis and classification," Bone Marrow Transplantation (2008) 41, S58-S64. Bouchlaka, M. N., "Immunotherapy following hematopoietic stem cell transplantation: potential for synergistic effects," Immunotherapy. 2010 May; 2(3): 399-418.

Monoclonal Antibodies (mAbs)

Monoclonal antibodies are useful in the treatment of various cancers. mAb cancer treatments utilize natural immune system functions to attack cancerous cells. Administration of mAbs specific for tumor antigens can be useful in targeting the tumor cells for destruction by the immune system. In some cases mAbs can trigger lysis of cancer cells, block cancer cell growth/replication, prevent angiogenesis, act as checkpoint inhibitors, and in some cases act to bind a tumor antigen while also activating specific immune cells. In some embodiments, a monoclonal antibody is monospecific. In some embodiments, a monoclonal antibody is bispecific. In some embodiments, a monoclonal antibody is a checkpoint inhibitor. In some embodiments, a mAb may be used in combination with CAR-T therapy.

When activated by therapeutic monoclonal antibodies, T-cell surface receptors can cause CRS. In some embodiments, antibodies which may induce CRS include anti-CD3 antibodies, anti-CD20 antibodies, anti-CD28 antibodies, anti-CTLA-4 antibodies, anti-PD-1 antibodies, and anti-PD-L1 antibodies. In some embodiments, antibodies which may induce CRS include alemtuzumab, muromonab-CD3, rituximab, tosituzumab, CP-870,893, LO-CD2a/BTI-322, TGN1412, pembrolizumab, nivolumab, and ipilimumab.

EXAMPLES

Example 1: Determining Brequinar Levels in Plasma

Figure 4:
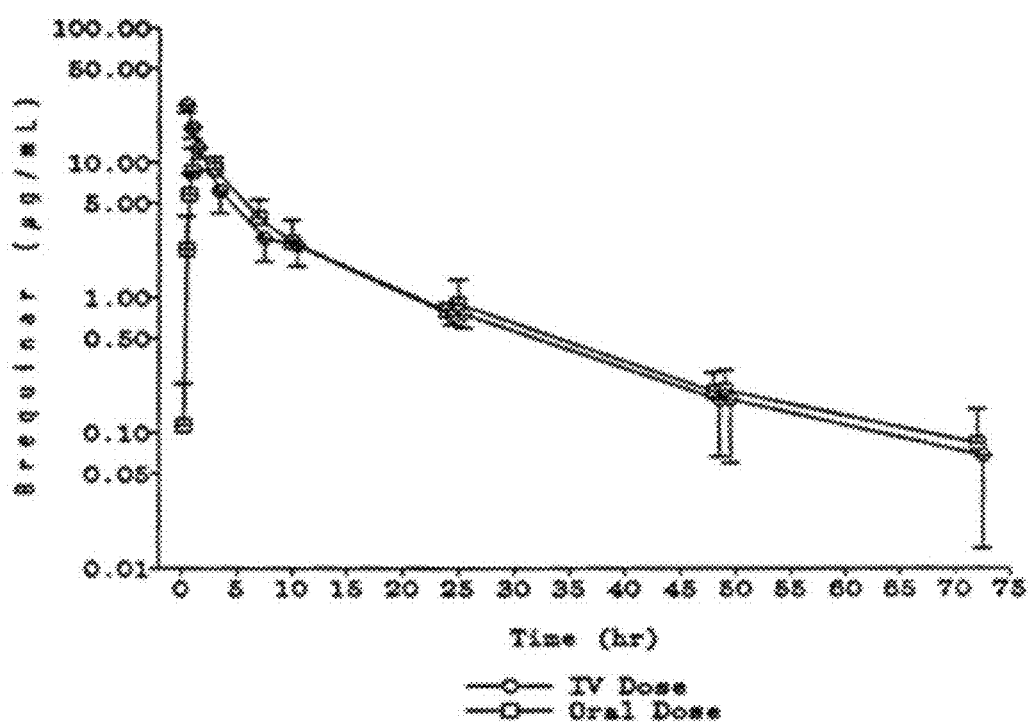
FIG. 4 is a scatter plot illustrating the concentration of brequinar in subject plasma over time when administered twice weekly.

FIG. 4 is a scatter plot illustrating the concentration of brequinar in subject plasma over time when administered twice weekly.

Figure 5:
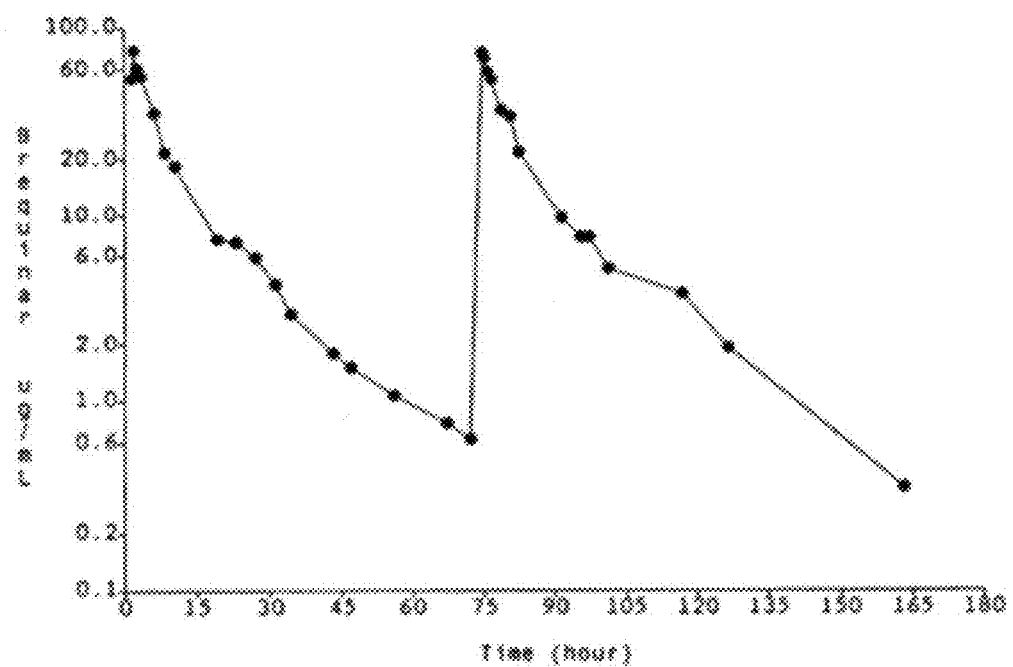
FIG. 5 is a scatter plot illustrating the bioavailability of an IV formulation of brequinar as compared to an oral dosage form.

FIG. 5 is a scatter plot illustrating the bioavailability of an IV formulation of brequinar as compared to an oral dosage form.

The concentration of DHO in a subject's plasma is correlated with the concentration of DHODH inhibitor in the plasma. As provided herein, the disclosed methods provide, in some embodiments, administering the DHODH inhibitor when the DHO concentration in the plasma is either at least a particular efficacy threshold or below a potential toxic threshold (i.e., a pre-determined level).

Figure 6:
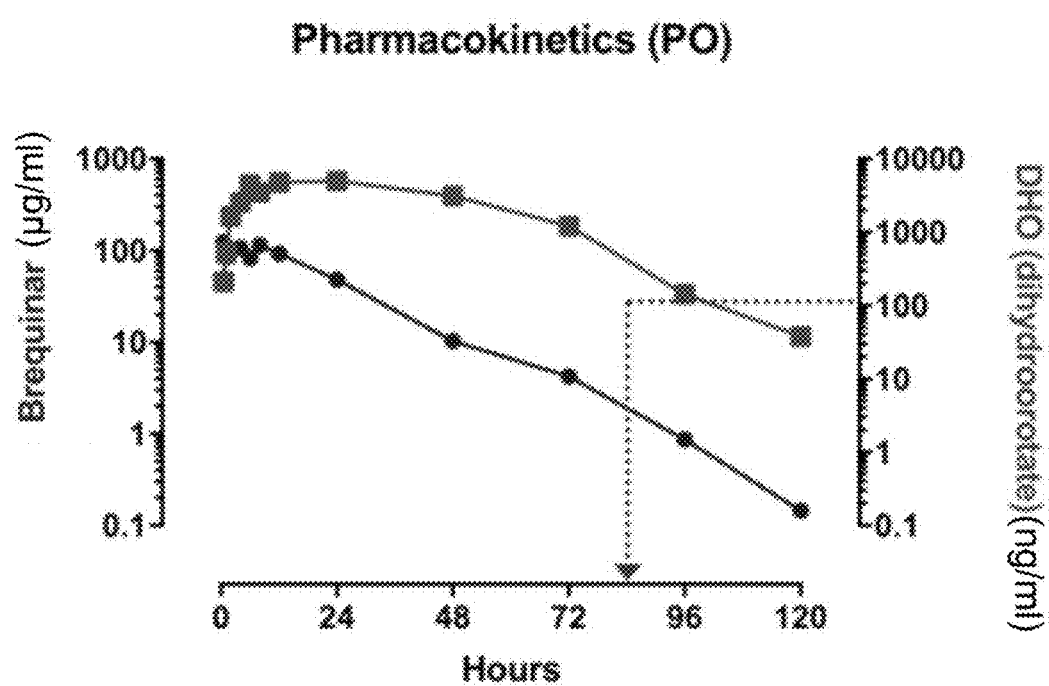
FIG. 6 is a scatter plot illustrating the concentration of brequinar in mice at a dose of 50 mg/kg over time.

FIG. 6 is a scatter plot illustrating the concentration of brequinar in mice at a dose of 50 mg/kg over time. The dashed line illustrates that about 100 ng/mL concentration of DHO remains in the plasma at about 84 hours.

Example 2: Adverse Events Observed in Subjects Receiving Brequinar

Brequinar was administered intravenously to 209 subjects once a week with a median number of doses per patient of 4 (range 1 to 24) at a median dose of 1200 mg/m$^2$ (range 588 to 3110). Adverse events that were observed in more than 3% of subjects are reported in Table 4, below:

TABLE 4

| | No. of Patients | Percent | No. of Patients Experiencing the AE, 5 y Max Grade | | | |
|---|---|---|---|---|---|---|
| | | | 1 | 2 | 3 | 4 |
| All Body Systems | 202 | 95.7 | 36 | 76 | 55 | 35 |
| Thrombocytopenia | 94 | 45.0 | 26 | 31 | 16 | 21 |
| Nausea | 91 | 43.5 | 59 | 19 | 12 | 1 |
| Anemia | 90 | 43.1 | 14 | 48 | 23 | 5 |
| Diarrhea | 77 | 36.8 | 43 | 21 | 10 | 3 |
| Vomit | 73 | 34.9 | 32 | 24 | 12 | 5 |
| Leukopenia | 69 | 33.0 | 26 | 31 | 10 | 2 |
| Stomatitis | 60 | 28.7 | 32 | 20 | 7 | 1 |
| Rash | 53 | 25.4 | 26 | 15 | 9 | 3 |
| Mucositis | 52 | 24.9 | 23 | 15 | 11 | 3 |
| Granulocytopenia | 37 | 19.6 | 16 | 17 | 3 | 5 |
| Fatigue | 33 | 15.8 | 23 | 8 | 2 | 0 |
| Pain Inject Site | 24 | 11.5 | 24 | 0 | 0 | 0 |
| Anorexia | 15 | 7.2 | 11 | 3 | 1 | 0 |
| Fever | 11 | 5.3 | 4 | 7 | 0 | 0 |
| Constipation | 10 | 4.8 | 6 | 2 | 1 | 0 |
| Somnolence | 9 | 4.3 | 7 | 2 | 0 | 0 |
| Pain, Abdominal | 8 | 3.8 | 4 | 3 | 1 | 0 |
| Dyspepsia | 7 | 3.3 | 6 | 1 | 0 | 0 |
| Headache | 7 | 3.3 | 4 | 3 | 0 | 0 |
| Infection | 7 | 3.3 | 4 | 3 | 0 | 0 |

Example 3: Determining DHO Levels in Plasma Samples Using DHO as a Standard

Prior to analysis the plasma samples are deproteinized by centrifugation through a 50 kD Amicon ultrafilter. 10 µL of a plasma sample is spiked with 5 µL of a standard solution of (S)-4,5-dihydroorotic-4,5,6-carboxy-$^{13}$C4 acid ($^{13}$C4-DHO) and then diluted with 35 µL of 0.1% (w/w) formic acid. Samples are injected into a reverse-phase 4 µm C18 column (Synergy Hydro RP-80A, 3 µm, 150×3 mm; Phenomenex, Australia). Chromatography is performed at 30° C. with a total flow rate of 0.3 mL/min, using solvent A (aqueous 5 mM ammonium acetate, 0.05% (w/v) formic acid) and solvent B (0.05% (w/v) formic acid in methanol) in a linear gradient elution from A:B 98:2 (v/v) to 85:15 (v/v) over 11 minutes, the 40:60 (v/v) for 1 minute, before returning to initial conditions for a further 6 minutes of equilibration.

Tandem mass spectrometry (LC/MS/MS) is performed using an Applied Biosystems API 4000 QTRAP mass spectrometer equipped with a Turbo-V-Spray source with the gas temperature set at 500° C. The source operated an electrospray interface (ESI) with switching ionization polarity (between +5000 V and −4000 V) during the run (18 min). The eluent is monitored by specific ion transitions for DHO and the internal standard. All data is quantified using Applied Biosystems software.

Example 4: Determining DHO Acid levels in Plasma Samples Using Orotic Acid as a Standard Prior to analysis the plasma samples are deproteinized by centrifugation through a 50 kD Amicon ultrafilter. 10 µL of a plasma sample is spiked with 5 µL of a standard solution of 15N2-orotic acid and then diluted with 35 µL of 0.1% (w/w) formic acid. Samples are injected into a reverse-phase 4 µm C18 column (Synergy Hydro RP-80A, 3 µm, 150×3 mm; Phenomenex, Australia). Chromatography is performed at 30° C. with a total flow rate of 0.3 mL/min, using solvent A (aqueous 5 mM ammonium acetate, 0.05% (w/v) formic acid) and solvent B (0.05% (w/v) formic acid in methanol) in a linear gradient elution from A:B 98:2 (v/v) to 85:15 (v/v) over 11 minutes, the 40:60 (v/v) for 1 minute, before returning to initial conditions for a further 6 minutes of equilibration.

Tandem mass spectrometry (LC/MS/MS) is performed using an Applied Biosystems API 4000 QTRAP mass spectrometer equipped with a Turbo-V-Spray source with the gas temperature set at 500° C. The source operated an electrospray interface (ESI) with switching ionization polarity (between +5000 V and −4000 V) during the run (18 min). The eluent is monitored by specific ion transitions for DHO and the internal standard. All data was quantified using Applied Biosystems SCIEX Multiquant software.

Example 5: Determined DHO Levels in Healthy Subjects and Cancer Patients

The concentration of dihydroorotic acid in human K2EDTA plasma samples was determined by reversed-phase high performance liquid chromatography with tandem mass spectrometric detection (LC-MS/MS). Plasma samples (50 µL) were spiked with 5 µL of a 1.0 µg/mL solution of (S)-4,5-dihydroorotic-4,5,6,carboxy-$^{13}C_4$ acid ($^{13}C_4$-DHO) in water, which was used as the internal standard (IS), then vigorously mixed with acetonitrile (200 µL) for 5 min. After centrifugation (12,000 rpm, 5 min), 150 µL of the supernatant was applied to a preconditioned Waters (Milford, Mass.) Oasis MAX solid phase extraction cartridge (1 cc, 30 mg). The cartridge was washed sequentially with water and methanol before eluting the analyte with 1% (v/v) formic acid in methanol (1 mL). The eluent was evaporated under a stream of nitrogen and reconstituted in 50 µL of 1% (v/v) formic acid in water. The solution was transferred into a conical bottom insert placed in an amber autosampler vial and sealed. A 10 µL aliquot of the solution was injected onto a Phenomenex (Torrance, Calif.) Synergi 4 µm Hydro-RP 80A HPLC column (250 mm×3.0 mm i.d.) preceded by an AQ C18 guard cartridge (4.0 mm×3.0 mm i.d.) and separated using an isocratic mobile phase composed of 0.05% (v/v) formic acid in water at a flow rate of 0.5 mL/min. An Agilent Technologies (Santa Clara, Calif.) model G6410B triple quadrupole mass spectrometer with an electrospray ionization interface was used for detection. Nitrogen was used as the nebulizing gas (30 p.s.i.) and drying gas (10 L/min, 350° C.). With a transfer capillary potential of 1,500 V, negative ions resulting from the m/z 157→113 transition for dihydroorotic acid and the m/z 161→117 transitions for the IS were measured by multiple reaction monitoring (dwell time, 150 msec; fragmentor potential, 70 V; collision energy, 4 V; collision cell accelerator voltage, 4 V). Quantitation was based upon integrating the extracted ion chromatograms for both transitions to provide peak areas and calculating the ratio of the analyte peak area to the IS peak area for each sample.

Table 5 provides data of DHO concentration for samples from certain random cancer patients, samples from healthy subjects, and samples from mice.

TABLE 5

| Subject No. | Sample | ASSAY DHO CONC. ng/mL | AVG. ASSAY CONC. ng/mL |
|---|---|---|---|
| Cancer Patients | | | |
| 1 | 1 | 4.1 | |
|   | 2 | 4.25 | 4.18 |
| 2 | 1 | 0 | |
|   | 2 | 0 | 0.00 |
| 3 | 1 | 1.17 | |
|   | 2 | 0.19 | 0.68 |
| 4 | 1 | 15.1 | |
|   | 2 | 15.4 | 15.25 |
| 5 | 1 | 5.2 | |
|   | 2 | 5.3 | 5.25 |
| 6 | 1 | 0.41 | |
|   | 2 | 0.86 | 0.64 |
| Healthy Subjects | | | |
| 1 | 1 | 0 | |
|   | 2 | 0 | 0.00 |
| 2 | 1 | 0 | |
|   | 2 | 0 | 0.00 |
| 3 | 1 | 0 | |
|   | 2 | 0 | 0.00 |
| 4 | 1 | 0 | |
|   | 2 | 0 | 0.00 |
| 5 | 1 | 0 | |
|   | 2 | 0 | 0.00 |
| 6 | 1 | 0 | |
|   | 2 | 0 | 0.00 |
| Mice | | | |
| 1 | 1 | 1 | 1 |
|   | 2 | 0.06 | 0.00 |

Table 6 provides patient data for 20 anonymous cancer patients whose DHO acid concentration was measured.

TABLE 6

| No. | Diagnosis | Sample | Gender | Age | Form and Stage | Chemotherapy | Blast Cells by Morphology* | Inunmio-phenotyping CD34+* | Inunmio-phenotyping CD19+/CD5+* | Cytogenetics |
|---|---|---|---|---|---|---|---|---|---|---|
| 1 | AML | Blood & Marrow | F | 60 | M0 or M5a | | | 12.6 (BM) | | 45, XX, −3, der(5)t(5; 3)(q13; ql2), −7, inv(12)(p 11, 2q24.1), dic(13; 22)(p 12; p 12), +l~2mar[8]/46, XX1121 |
| 2 | AML | | | | | | | | | |
| 3 | AML | Blood | M | 84 | Untreated | | 30-40 (BM) | 1.64 (PB)/43.1 (BM) | | |
| 4 | AML | | | | | | | | | |
| 5 | AML | | | | | | | | | |
| 6 | AML | Blood | M | 35 | | Tretinoin | 65 (PB)/43 (BM) | 39 (PB) | | |

TABLE 6-continued

| No. | Diagnosis | Sample | Gender | Age | Form and Stage | Chemotherapy | Blast Cells by Morphology* | Inunmio-phenotyping CD34+* | Inunmio-phenotyping CD19+/CD5+* | Cytogenetics |
|---|---|---|---|---|---|---|---|---|---|---|
| 7 | AML | Blood | F | 37 | M3 | Tretinoin Idarubicin Arsenic trioxide | 75 (PB)/ 79 (BM) | 0.1 | | |
| 8 | AML | Blood | M | 68 | | | 60 (BM) | 11 (PB) | | |
| 9 | AML | Blood | M | 70 | | | 76 (BM) | 97 (PB) | | ish(D7Zlx2, D7S486xl)[41/200], (KAT6Ax3)[461/500], (D8Z2, MYC)x3 [186/200], (RLINXlTlx3)[461/5001 |
| 10 | AML | Blood & Marrow | F | 57 | Relapsed | Retinoic acid, Arsenic, Idarubicin, Arsenic | 0 (PB)/ 11 (BM) | 0.7 (PB) | | t(15; 17) PML/RARA fusion [by FISH]) Abnormal 918" |
| 11 | AML | Blood | M | 65 | non promyelocytic with monocytic differentiation | | 38 (BM) | 0.77 (PB) | | FLT3/NPM1 mutations |
| 12 | CLL | Blood & Marrow | M | 53 | | | | | 97 (PB)/ 91 (BM) | |
| 13 | CLL | Blood | M | 75 | Relapsed | | | | 85 (PB)/ 75 (BM) | 7.5% have del[13q/14]-specific signal |
| 14 | CLL | Blood & Marrow | F | 56 | Relapsed refractory | Rituxan | | | 27.7 (PB)/ 67.5 (BM) | |
| 15 | CLL | Blood & Marrow | F | 67 | Relapsed | | | | 53.4 (PB)/ 61.4 (BM) | |
| 16 | CLL | Blood | F | 69 | | | | | 3.73 (PB) | |
| 17 | CML | | | | | | | | | |
| 18 | CML | Blood & Marrow | M | 50 | Newly Diagnosed, Chronic Phase | | | 0.8 (PB)/ 1.4 (BM) | | BCR-ABL positive |
| 19 | CML | Blood & Marrow | M | 31 | Relapsed refractory | BCR-ABL, Gleevec | | 0.72 (PB)/ 7.1 (BM) | | |
| 20 | CML | Blood & Marrow | M | | Newly diagnosed chronic phase | N/A | | 1.6 (PB)/ 1.8 (BM) | | BCR-ABL positive |

*(PB = % Blood, BM % Marrow)

Table 7 provides baseline endogenous DHO acid concentration in plasma samples from the set of 20 cancer patients.

TABLE 7

| No. | Assay 1 | Assay 2 | Assay 3 | Mean |
|---|---|---|---|---|
| 1 | <LOD | <LOD | | <LLQ |
| 2 | 13.8 | 15.2 | | 14.5 |
| 3 | 58.1 | 49.0 | | 53.6 |
| 4 | 32.8 | 30.0 | | 31.4 |
| 5 | <LOD | <LLQ | | <LLQ |
| 6 | 9.5 | 8.4 | | 8.99 |
| 7 | <LLQ | <LLQ | | <LLQ |
| 8 | 18.0 | 16.4 | | 17.2 |
| 9 | 6.7[b] | 33.4 | 29.9 | 31.6 |
| 10 | 12.8 | 13.9 | | 13.4 |
| 11 | 17.0[b] | 11.8 | 10.2 | 11.0 |
| 12 | <LOD | <LOD | | <LLQ |
| 13 | <LOD | <LOD | | <LLQ |
| 14 | <LOD | <LOD | | <LLQ |
| 15 | 6.51 | 5.14 | | 5.83 |
| 16 | <LLQ | <LLQ | | <LLQ |
| 17 | 37.1[b] | <LOD | <LOD | <LLQ |
| 18 | <LOD | <LLQ | | <LLQ |
| 19 | <LOD | <LOD | | <LLQ |
| 20 | 5.1[b] | <LLQ | <LLQ | <LLQ |

[a]<LOD, below the limit of detection (analyte peak not distinguishable from baseline); <LLQ, assayed concentration below the lower limit of quantitation (5.0 ng/mL).
[b]Result not used for calculation of the mean assayed concentration and percent difference.

Figure 7:
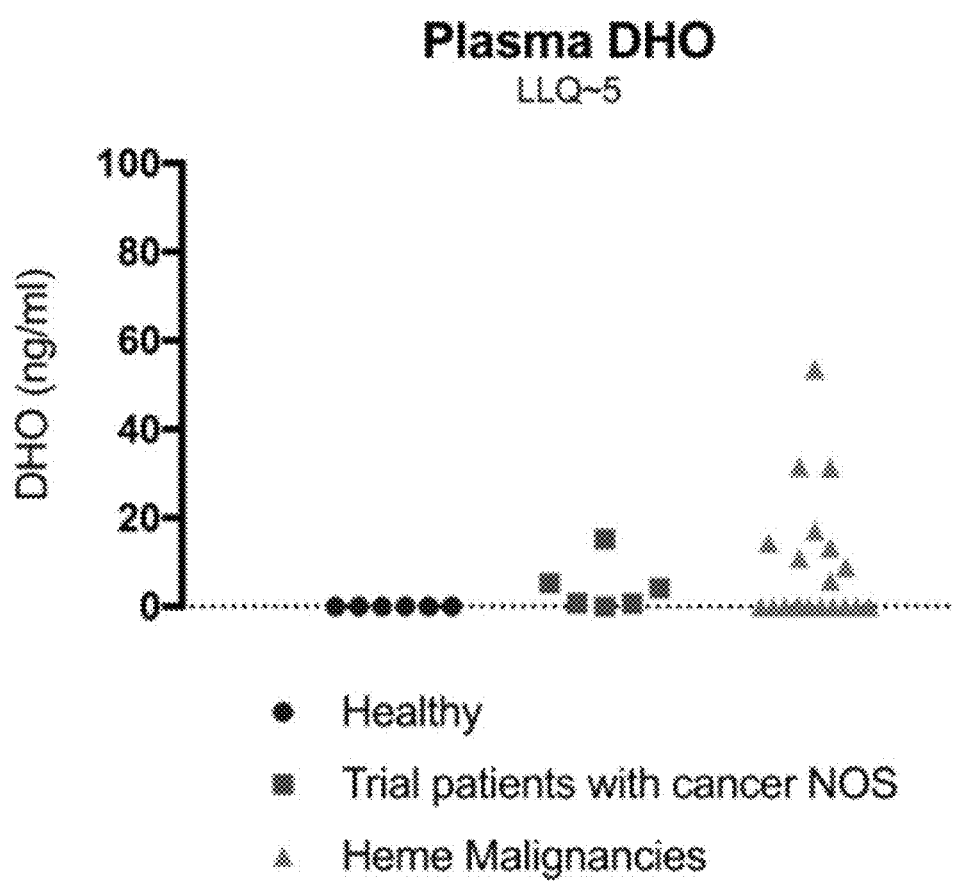
FIG. 7 is a scatter plot illustrating the baseline DHO levels in random cancer patients and healthy patients, as reported in Table 5.

FIG. 7 is a scatter plot illustrating the baseline DHO levels in random cancer patients and healthy patients, as reported in Table 5.

Example 6: Clinical Dosing Regimens Previously Tested for Brequinar in Patients with Refractory Solid Tumors Previous clinical dosing regimens assessed brequinar for use in treating refractory solid tumors in patients. For example, Arteaga reported administration of brequinar as "single daily i.v. bolus over a 5-day period repeated every 28 days." Arteaga, et al., "Phase I clinical and pharmacokinetic trial of Brequinar sodium (DuP 785; NSC 368390)," Cancer Res., 49(16):4648-4653 (Aug. 15, 1989). Specifically, Arteaga administered "[o]ne hundred seven courses of treatment at dosages ranging from 36 to 300 mg/m$^2$/day×5" to 45 patients (31 male and 14 female) with refractory solid tumors. The reported median age of these patients was 58 years (range 30-74); and the median Southwest Oncology Group performance status was reported to be 1 (range, 0-3). Arteaga found "[f]or the daily×5 i.v. schedule, the recommended dose of Brequinar for phase II evaluation is 250 mg/m$^2$ for good risk patients and 135 mg/m$^2$ for poor risk patients."

Burris reported "investigating the pharmacokinetic and toxicity of brequinar in combination with cisplatin" where patients were initially treated with weekly brequinar, in combination with an every-three-week administration of cisplatin. See Burris, et al., "Pharmacokinetic and phase I studies of brequinar (DUP 785; NSC 368390) in combination with cisplatin in patients with advanced malignancies," Invest. New Drugs, 16(1):19-27 (1998). Burris found that "due to toxicity, the schedule was modified to a 28-day cycle with brequinar given on days 1, 8, 15, and cisplatin on day 1." A total of 24 patients (16 male, 8 female; median age 57; median performance status 1) received 69 courses of therapy. Six dose levels were explored, with cisplatin/brequinar doses, respectively, of 50/500, 50/650, 50/860, 60/860, 75/650, and 75/860 mg/m². Burris concluded that "full dose of 75 mg/m² cisplatin (day 1) can be administered with 650 mg/m² brequinar (days 1, 8 and 15) without significant modifications of individual drug pharmacokinetic parameters."

Noe reported "in vitro and in vivo studies [of brequinar] demonstrate the superiority of prolonged drug exposure in achieving tumor growth inhibition. This phase I study evaluated the administration of brequinar sodium by short, daily i.v. infusion for 5 days repeated every 4 weeks." See Noe, et al., "Phase I and pharmacokinetic study of brequinar sodium (NSC 368390)," Cancer Res., 50(15):4595-4599 (1990). Noe examined "Wifty-four subjects . . . received drug in doses ranging from 36-300 mg/m²." Noe found that "[t]he maximum tolerated dose on the 'daily times 5' schedule was 300 mg/m²" and that "[t]he recommended phase II dose is 250 mg/m²." Noe concluded that "pharmacodynamic analysis of the day 1 kinetic parameters and the toxicities occurring during the first cycle of drug therapy revealed significant correlations between mucositis and dose, AUC, and peak brequinar concentration; between leukopenia and AUC and peak drug concentration; and between thrombocytopenia and beta elimination rate."

Schwartsmann reported dosing brequinar in 43 patients who "received 110 courses of Brequinar sodium by short-term intravenous (i.v.) infusion" every 3 weeks." See Schwartsmann, et al., "Phase I study of Brequinar sodium (NSC 368390) in patients with solid malignancies," Cancer Chemother. Pharmacol., 25(5):345-351 (1990). Schrwatsmann based dose escalation on "a modified Fibonacci scheme," initially, but relied on a pharmacologically guided dose escalation after PK data became available, noting that "at toxic levels, dose escalation was applied on the basis of clinical judgement." Swchwartsmann reported that "[t]he maximum tolerable doses for poor- and good-risk patients were 1,500 and 2,250 mg/m², respectively. One mixed response was observed in a patient with papillary carcinoma of the thyroid. The recommended doses for phase II studies are 1,200 and 1,800 mg/m² Brequinar sodium, given by a 1-h i.v. infusion every 3 weeks to poor- and good-risk patients, respectively."

Example 7: Exemplary Clinical Dosing in Accordance with the Present Disclosure

Inclusion Criteria

The following are proposed inclusion criteria for subjects in a proposed clinical trial:
Willing and able to provide written informed consent for the trial.
Adults, 18 years of age and older, with pathologically confirmed, relapsed or refractory acute myelogenous leukemia.
≥18 years of age on day of signing informed consent
ECOG Performance Status 0 to 2.
Cardiac ejection fraction ≥40%
Adequate hepatic function (unless deemed to be related to underlying leukemia)
Direct bilirubin ≤2×ULN
ALT≤3×ULN
AST≤3×ULN
Adequate renal function as documented by creatinine clearance ≥30 mL/min based on the Cockcroft-Gault equation
In the absence of rapidly proliferative disease, the interval from prior leukemia directed therapy to time of study initiation will be at least 7 days for cytotoxic or non-cytotoxic (immunotherapy) agents. Hydrea is allowed up to 48 hours prior to the first dose for patients with rapidly proliferative disease.
The effects of brequinar on the developing human fetus are unknown. For this reason, women of child-bearing potential and men must agree to use adequate contraception (hormonal or barrier method of birth control; abstinence) prior to study entry and for the duration of study participation. Should a woman become pregnant or suspect she is pregnant while she or her partner is participating in this study, she should inform her treating physician immediately. Men treated or enrolled on this protocol must also agree to use adequate contraception prior to the study, for the duration of study participation, and for 90 days after completion of brequinar administration.
Male subjects must agree to refrain from sperm donation from initial study drug administration until 90 days after the last dose of study drug.

Exclusion Criteria

The following are proposed exclusion criteria for excluding a subject in the study.
White blood count >25×109/L (note: hydroxyurea is permitted to meet this criterion).
Any concurrent uncontrolled clinically significant medical condition, laboratory abnormality, or psychiatric illness that could place the participant at unacceptable risk of study treatment.
QTc interval using Fridericia's formula (QTcF)≥470 msec. Participants with a bundle branch block and prolonged QTc interval may be eligible after discussion with the medical monitor.
The use of other chemotherapeutic agents or anti-leukemic agents is not permitted during study with the following exceptions:
Intrathecal chemotherapy for prophylactic use or maintenance of controlled CNS leukemia.
Use of hydroxyurea may be allowed during the first 2 weeks of therapy if in the best interest of the participant and is approved by the medical monitor.
AML relapse less than 6 months following stem cell transplantation.
Presence of graft versus host disease (GVHD) which requires an equivalent dose of ≥0.5 mg/kg/day of prednisone or therapy beyond systemic corticosteroids (e.g. cyclosporine or other calcineurin inhibitors or other immunosuppressive agents used for GVHD).
Active cerebrospinal involvement of AML.
Diagnosis of acute promyelocytic leukemia (APL)
Clinically active hepatitis B (HBV) or hepatitis C (HCV) infection.
Severe gastrointestinal or metabolic condition that could interfere with the absorption of oral study medication
Prior malignancy, unless it has not been active or has remained stable for at least 5 years. Participants with treated non-melanoma skin cancer, in situ carcinoma or cervical intraepithelial neoplasia, regardless of the disease-free duration, are eligible if definitive treatment for the condition has been completed. Participants with organ-confined prostate cancer with no evidence of recurrent or progressive disease are eligible if hormonal therapy has been initiated or the malignancy has been surgically removed or treated with definitive radiotherapy.

Nursing women or women of childbearing potential (WoCBP) with a positive urine pregnancy test.

Dose Levels

Proposed dosing levels are provided below:

Patients are dosed every 3.5 days. An example schedule of events is reported in Table 8.

TABLE 8

| Procedures[a] | Screen[b] | Cycle 1 (Study Days 1-14) | | | | | Dose Escalation Cycle (Cycle 2 and beyond as needed) | | Maintenance Dose (no dose adjustment) Every 2 weeks | Final Visit | F/U Phone Call Final Visit + 2 wks | Survival |
| --- | --- | --- | --- | --- | --- | --- | --- | --- | --- | --- | --- | --- |
| | | Day 1 | Day 2 | Day 3 | Day 4 | Day 8 | Day 1 | Day 8 | Day 1 | | | |
| Informed Consent | X | | | | | | | | | | | |
| AE/Concomitant Medication Assessment | X | X | X | X | X | X | X | X | X | X | X | |
| Demographics[c] | X | | | | | | | | | | | |
| Physical Exam (including weight) | X | X | | | | | X | | X | X | | |
| Vital Signs[c] | X | X | | | | X | X | X | X | X | | |
| Pregnancy Test[d] | X | | | | | | | | X | X | | |
| ECOG Performance Status | X | | | | | | | | | | | |
| Hematology/Chemistry[e] | X | X | | | | X | X | X | X | X | | |
| Chromosomal & mutational testing[f] | X | | | | | | | | | | | |
| 12-lead ECG | X | | | | | | | | X | X | | |
| MUGA/Echocardiogram | X | | | | | | | | | | | |
| Bone Marrow Aspirate[g] | X | | | | | | X | | X[g] | X | | |
| Brequinar/DHO Plasma Sample[h] | | X | X | X | X | X | X | X | X | X | | |
| Ship Plasma Samples | | | | | | X | | X | X | | | |
| Dispense/Collect Study Medication | | X | | | | | X | | X | X | | |
| Dispense/Collect Subject Calendar/Diary | | X | | | | | X | | X | X | | |
| Survival Assessment | | | | | | | | | | | | X |

[a]Visit window of ±1 day for dose escalation cycles; window of ±3 days for non-dose-escalation cycles.
[b]Obtain informed consent prior to performing any screening or study-specific procedures. Screening procedures must be performed within 14 days prior to initial study drug administration. Procedures at C1D1 that are repeats of Screening may be omitted if <72 h since Screening assessment.
[c]Demographic information includes date of birth, height, weight, race, and ethnic origin. Vital signs include heart rate, respiratory rate, seated blood pressure, oral/aural body temperature.
[d]For women of childbearing potential only.
[e]CBC differential may be omitted if previous WBC < 0.5 × 10$^9$/L
[f]Per institutional standard of care.
[g]Local bone marrow aspirate testing will include molecular testing, flow cytometry for minimal residual disease counts (MRD); perform bone marrow aspirations once every 2 weeks while dose adjustments are ongoing and once every 12 weeks after a stable dose has been reached. Only the Day 42 sample will be used to assess hematological toxicity. Ship sample to central lab for future testing. Timing of this procedure may be adjusted to ensure results are available for the next clinic visit.
[h]Brequinar/DHO plasma sampling schedule: Cycle 1: 0 (pre-dose), post dose 1, 2, 4, 6, 24, 48, 72 hours and C1D8 pre-dose (+84 h after C1D4 dose); Cycle 2 and adjustment cycles: pre-dose Days 1 and 8. Maintenance dose: Day 1 pre-dose. Day 1 PK window ±15 minutes through 6 h draw, window for additional C1 draws ±2 h; window for Cycle 2 and beyond plasma brequinar/DHO draws ±4 h. Plasma samples for brequinar/DHO for expansion cohort are to be obtained prior to dosing on Day 1 of each 2-week cycle.

Another example dosing schema is:

| Dose level | Brequinar (mg/m$^2$) |
| --- | --- |
| +2 (Target dose) | 800 |
| +2 (Target dose) | 650 |
| 0 (Starting dose) | 500 |
| −1 | 425 |

The dosing sequence (i.e. every 3.5 days) will be subject to revision after review of preliminary efficacy, toxicity, and PK data within this clinical trial. PK data from patients treated at dose level 0 will be used to evaluate the anticipated minimally effective dose, to adjust the dose and schedule, if necessary, in subsequent dose level cohorts.

Example 8: Optimized Dosage Based on DHO Levels

Figure 8:
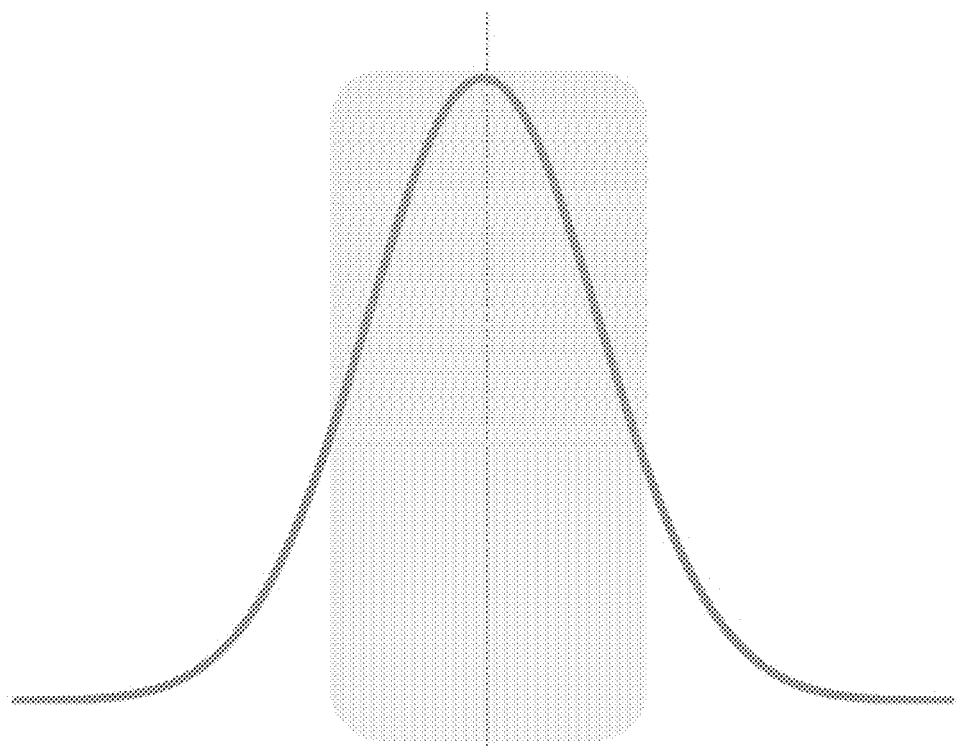
FIG. 8 is a graph showing the therapeutic benefit of a drug, such as brequinar, that targets a metabolic pathway as a function of levels of DHO.

FIG. 8 is a graph showing the therapeutic benefit of a drug, such as brequinar, that inhibits DHODH as a function of levels of DHO. On the left side of the graph, levels of the DHO are below a minimum threshold, and target engagement of the drug is insufficient to have a therapeutic effect. In the grey region of the graph, levels of DHO are above a minimum threshold but below a maximum threshold, so the drug has sufficiently engaged its target to provide a thera-

47 peutic effect but has not caused effects that are deleterious to healthy cells. On the right side of the graph, levels of DHO are above the maximum threshold, and the effects of the drug cause harm to healthy cells. Adjustments to the dosing regimen based on the relationship between therapeutic benefit and metabolite levels are illustrated in Table 9.

TABLE 9

| Metabolite level | Adjustment to dosing regimen |
|---|---|
| below minimum threshold | increase dosage, frequency of dose of administration, or both |
| above minimum threshold but below maximum threshold | no change |
| above maximum threshold | decrease dosage, frequency of dose administration, or both |

Example 9: Effect of Brequinar-Containing Composition on Patient with AML

The effect of a composition containing brequinar was analyzed on first patient a with acute myeloid leukemia (AML). After administration of a dose of the composition, the patient achieved a DHO plasma level threshold of 1,600 ng/mL in less than 24 hours and remained above that threshold for 84 hours. This patient showed a positive response as indicated by reduction in bone marrow blast count, improvement of extramedullary hematopoiesis, and shift to more differentiation in peripheral blasts.

Example 10: Effect of Brequinar-Containing Composition on Patient with AML

The effect of a composition containing brequinar was analyzed on second patient a with AML. After administration of a dose of the composition, the patient achieved a DHO plasma level threshold of 2,900 ng/mL in less 24 hours and remained above that threshold for 84 hours. This patient showed a positive response to the disease with a lowering of peripheral blasts and increase in absolute neutrophil count, along with greater differentiation of peripheral blasts.

Example 11: Effect of Brequinar-Containing Composition on Patient with AML

The effect of a composition containing brequinar was analyzed on second patient a with AML. After administration of a dose of the composition, the patient achieved a DHO plasma level threshold of 133 ng/mL in less than 2 hours and remained above that threshold for 84 hours. This patient showed a positive response as indicated by a trend towards differentiation of his peripheral blasts.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of making a 2-(2'-halo-1-1'-biphenyl-4-yl)-quinoline carboxylic acid, the method comprising:
   incubating a compound of formula (I) with a compound of formula (II) in a mixture comprising a base at a temperature of from 60° C. to 70° C. for from 15 hours to 30 hours; and
   adding an acid, to the mixture, thereby creating a compound of formula (III) according to following reaction:

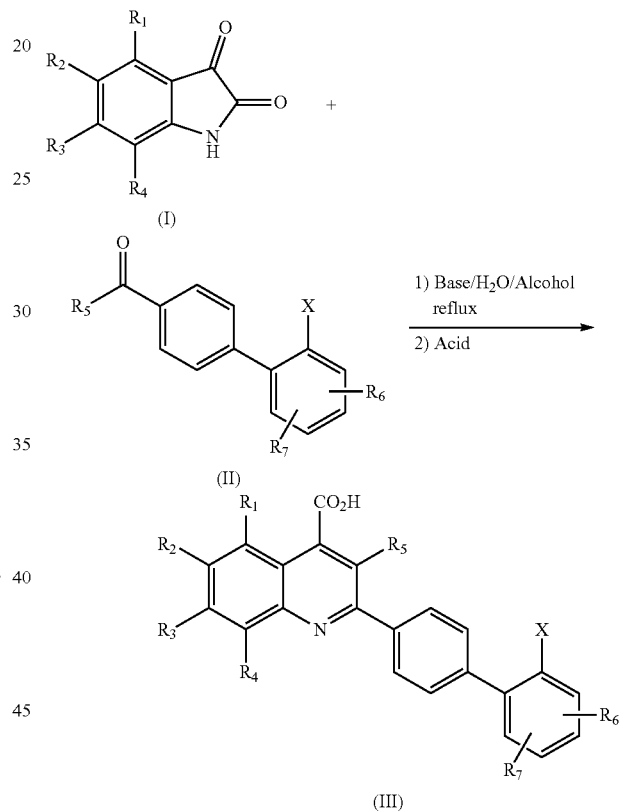

wherein:
$R_1$, $R_2$, $R_3$, and $R_4$ are independently H, F, Cl, Br, I, $CH_3$, $CF_3$, $SCH_3$ or $CH_2CH_3$, at least two of $R_1$, $R^2$, $R_3$, and $R_4$ being H;
$R_5$ is H, alkoxy of 1-3 carbon atoms, or alkyl of 1-2 carbon atoms;
$R_6$ and $R_7$ are independently H, F, Cl, Br, alkyl of 1-5 carbon atoms, $NO_2$, OH, $CF_3$ or $OCH_3$;
X is a halogen.

2. The method of claim 1, wherein the incubating step comprises the mixture comprising a molar ratio of the base to the compound of formula (II) of from about 5:1 to about 8:1.

3. The method of claim 1, wherein the yield of the compound of formula (III) is at least 80%.

4. The method of claim 1, wherein the base is selected from the group consisting of KOH, NaOH, and $NH_4OH$.

5. The method of claim 1, wherein the acid is selected from the group consisting of HCl and acetic acid.
6. The method of claim 1, wherein the compound of formula (III) has a structure represented by formula (IV):
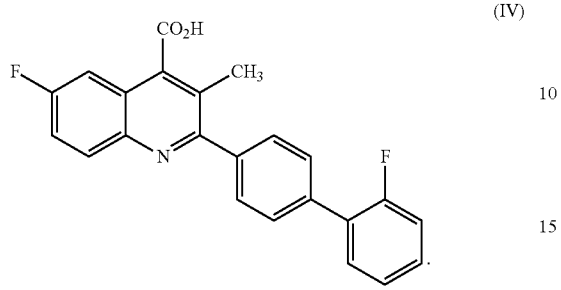
(IV)
* * * * *